(12) United States Patent
Denesuk et al.

(10) Patent No.: US 7,137,358 B2
(45) Date of Patent: Nov. 21, 2006

(54) AMUSEMENT ARTICLES POSSESSING MICROBE-INHIBITING PROPERTIES

(75) Inventors: Matthew Denesuk, Tucson, AZ (US); Eugenie V. Uhlmann, Tucson, AZ (US)

(73) Assignee: Seefar Technologies, Inc., Tucson, AZ (US)

( * ) Notice: Subject to any disclaimer, the term of this patent is extended or adjusted under 35 U.S.C. 154(b) by 588 days.

(21) Appl. No.: 09/872,500

(22) Filed: Jun. 1, 2001

(65) Prior Publication Data
US 2001/0027755 A1 Oct. 11, 2001

Related U.S. Application Data

(62) Division of application No. 09/059,826, filed on Apr. 14, 1998, now Pat. No. 6,240,879.

(60) Provisional application No. 60/043,014, filed on Apr. 15, 1997.

(51) Int. Cl.
*A01K 29/00* (2006.01)
(52) U.S. Cl. ...................................................... 119/709
(58) Field of Classification Search ................ 119/702, 119/709, 28.5, 169, 526, 652; 5/690, 636, 5/653, 652, 698
See application file for complete search history.

(56) References Cited

U.S. PATENT DOCUMENTS

| 4,712,510 A | * | 12/1987 | Tae-Ho ........................ 119/708 |
| 4,766,113 A | * | 8/1988 | West et al. .................. 514/187 |
| 5,111,771 A | * | 5/1992 | Mathews ..................... 119/708 |
| 5,233,787 A | * | 8/1993 | Andersen .................... 119/28.5 |
| 5,554,373 A | * | 9/1996 | Seabrook et al. ............ 424/400 |
| 5,560,319 A | | 10/1996 | Rising |
| 5,560,320 A | * | 10/1996 | Plunk .......................... 119/709 |
| 5,856,005 A | * | 1/1999 | Gurian ......................... 428/370 |
| 5,868,933 A | | 2/1999 | Patrick et al. |
| 5,885,543 A | * | 3/1999 | Klatte ........................ 210/754 |
| 5,945,215 A | * | 8/1999 | Bersted et al. .............. 428/364 |
| 6,153,036 A | * | 11/2000 | Williamson et al. ........ 156/148 |
| 6,210,508 B1 | * | 4/2001 | Williamson et al. ........ 156/148 |
| 6,240,879 B1 | * | 6/2001 | Denesuk et al. ............ 119/709 |
| 6,287,408 B1 | * | 9/2001 | Williamson et al. ........ 156/148 |

FOREIGN PATENT DOCUMENTS

| GB | 2 182 857 | * | 5/1987 |
| GB | 1384775 | | 11/1991 |
| GB | 2248774 | | 11/1991 |

OTHER PUBLICATIONS

Affidavit of Dennis Curley of Lazy Pet, Dated May 29, 1997, 2 Pages.

(Continued)

*Primary Examiner*—Thomas Price
(74) *Attorney, Agent, or Firm*—McGarry Bair PC

(57) ABSTRACT

An amusement article for a domestic animal comprising an outer textile casing defining a shape in the form of a small article which can be carried by a domestic animal, an inner filling, and a microbe-inhibiting agent or property applied to at least one of the outer textile casing and the inner filling. The toys may be fabricated in various shapes, designs and styles, e.g., animals, bones, hearts, geometric shapes, etc. A process for applying the microbe-inhibiting agent or property to at least one of the outer textile casing and the inner filling is provided. Application methods include spraying, dipping, brushing, and rolling the microbe-inhibiting agent or property onto at least one of the outer textile casing and the inner filling.

12 Claims, 3 Drawing Sheets

OTHER PUBLICATIONS

*Ultra-Fresh* Antimicrobials Brochure Undated, p. 1.
Typical *Ultra-Fresh* * Uses Brochure Undated, 1 Page.
Examples of Micro-Organisms That *Ultra-Fresh* * Products Inhibit Brochure Undated, 1 Page.
Examples of Antimicrobial Testing (*Ultra-Fresh*) Brochure Undated, 1 Page.
A Sample of Microbial Test Methods Available Brochure Undated, 1 Page.
Letter from Ron Tatar of Crain Industries, Inc. to Dennis Curley re: Anti-Microbial additives for suppliers Undated, 1 Page.
Letter from Ron Tatar of Crain Industries, Inc. to Dennis Curely re; Anti-Microbial Additives for Polyurethane Foam Undated, 1 Page.
Technical Data Sheet, *Ultra-Fresh* ® *DM-50* from Thomson Research Associates Undated, 4 Pages.
Antimircrobial Activity on Garments Undated, 2 Pages.
Milliguard, Retards the Growth of the Following Micro-Organisms Undated, 2 Pages.
Fortrel Bactishield, The Antimicrobial Fiber Brochure Undated, 2 Pages.
Letter from C. Kel Little of Precision Fabrics Group, Inc. to Luis Didonato, Subject: Antimicrobial Undated, 1 Page.
Aegis® High Density Brochure Undated, 1 Page.
Effects of Microbial Growth in the Skin, Uniform Fabric Environment Undated, 2 Pages.
A New, Durable Antimicrobial Finish for Textiles* Richard L. Gettings, Dow Corning Corp., and Benny L. Triplett, Burlington Industries, Undated, 4 Pages.
Letter from Mike Sanders, Vice Pres. of Cal-Pacific Dyeing & Finishing Corp., to Luis Didonato of Lazy Pet, and attached speck sheet on the Durable Bacteriostatic and Fungistatic agent Undated, 2 Pages.
Vinyzene® Antimicrobial Additives for Plastics, Product Information Morton Plastics Additives, Undated 2 Pages.
Vinyzene® , Material Safety Data Sheet Morton International, Inc., Dec. 18, 1996, 6 Pages.
Choose the Right Biocide to Meet Your Needs. Brochure on Cunilate® Morton Plastics Additives, Undated 5 Pages.
Bio-Pruf™ Treated Brochure Morton International, Inc. Undated, 8 Pages.
Ultra-Fresh Brochure Undated, 2 Pages.
*Ultra-Fresh* * Brochure Thomson Research Associates, Undated, 8 Pages.

* cited by examiner

AMUSEMENT ARTICLES POSSESSING MICROBE-INHIBITING PROPERTIES

CROSS-REFERENCE TO RELATED APPLICATION

This application is a divisional of U.S. patent application Ser. No. 09/059,826, filed Apr. 14, 1998 now U.S. Pat. No. 6,240,879, which claims the benefit of provisional patent application Ser. No. 60/043,014 filed Apr. 15, 1997.

BACKGROUND OF THE INVENTION

1. Field of The invention

This invention relates to an amusement article, principally for domestic animals, and more particularly, to an amusement article having a microbe-inhibiting agent or property that substantially inhibits the proliferation of microbes on, within, or around the amusement article. The term "microbe" herein refers broadly to classes of bacteria, viruses, germs, molds, mildews, fungi, allergens, and other microorganisms. An article of the present invention provides both comfort and health benefits to both pets and people involved with the use of such an article.

2. Description of the Related Art

Some conventional amusement articles for pets generally comprise a textile-based outer material and a filler material, e.g., fiberfill, foam, beads, etc. In addition, various types of noisemakers or materials such as catnip have also been associated with amusement articles.

The prior art amusement articles do not include a microbe-inhibiting agent or property, and therefore, do not address the problems that can arise if microbes are allowed to grow or proliferate on, within, or around the articles. A damp environment often encourages the proliferation of microbes. Because it is common for pets, especially dogs, to salivate upon, deposit partially digested food upon, urinate upon, or otherwise soil their amusement articles; and because such articles are generally porous and absorbent, microbial proliferation is especially problematic. The fact that the articles can remain at favorable incubation temperatures (e.g., in a dog's mouth or close to a dog's body while sleeping) further aggravates the problem. These conditions can also make the articles attractive to other pests such as fleas and ticks. Pets using such articles, as well as their owners, can thus be exposed to an increased health hazard. The environment to which such articles are exposed is unique; and the difficulty in designing and developing a product which is efficacious, safe, non-toxic, and economical is not easy to produce. This may explain why amusement articles for pets have not included a microbe-inhibiting agent or property.

Although the exteriors of pet articles can be washed, it is difficult to effectively wash the interior stuffed or filled articles. This is due to the difficulty of diffusing the cleaning agents into and out from the materials which comprise the article. Organic and inorganic nutrients for microbes, as well as microbes themselves, often remain after washing. Accordingly, there is a demand in the pet products industry for amusement articles which are microbe inhibiting in nature, promote good hygiene, are economical to manufacture, and are at the same time usable in their usual manner by the pets.

SUMMARY OF THE INVENTION

According to the invention, amusement articles for pets have an effective amount of a microbe-inhibiting agent or property that is effective in limiting microbial proliferation, and at the same time is not present in quantity, concentration or nature whereby the articles may be harmful to the pets or humans who come into contact with the articles. The effective amount of the microbe-inhibiting agent or property limits the spread of the microbe-inhibiting chemicals or agents within and about the article, and takes into consideration the patterns of use and material structure of the article.

According to the invention, a textile-based amusement article for a domestic animal comprises an outer textile casing formed of a tough, chew-resistant textile defining a shape in the form of a small article of a size which can typically be carried by a domestic animal, an inner filling and at least one of the outer textile casing and the inner filling having an effective micro-inhibiting agent or property. Typically, the article is in the form of an animal, a bone, a heart or a geometric shape. The weight of the article is typically less than 250 gm, although somewhat heavier articles can be made for bigger animals. Preferably, the outer textile casing is made from at least one fiber selected from the group consisting of acrylics, polyester, nylon, olefin polymers, triacetate polymers, rubber and spandex.

The outer textile casing can comprise a woven, a non-woven or a knit fabric made from natural or synthetic fibers. In one embodiment, the fabric comprises a high-pile component attached to a backing material to form an artificial fleece. Preferably, the articles are in the shape of an animal.

The inner filling for the article can comprise a number of different materials, including, a foam, a particulate material or a fibrous filling. The fibrous filling can be selected from the group consisting of polyolefins, acrylics, nylon, polyester, polyurethane, polyethylene terephthalate, celluous acetate, triacetate resin fibers and blends thereof. In one embodiment, the microbe-inhibiting agent or property is applied to at least a portion of the fibers in a fibrous filling for the article.

The microbe-inhibiting agent or property can be at least one of a microbe-cidal, microbe-starving and microbe-impenetrable agents. In one embodiment, a microbe-inhibiting agent in the form of a compound can be present in an effective amount depending on the nature of the product, but generally in the range of 0.5 to 10 percent by weight of the article. In another embodiment, the microbe-inhibiting agent is a compound selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, polysubstituted imine salts and phosphate esters, and mixtures thereof. Preferred compounds are chlorine dioxide, 2,4,4'-trichloro-2'-hydroxydiphenyl and the latter is incorporated into at least a portion of resin fibers which constitute the filling or the casing. In a preferred embodiment the filling comprises acrylic fibers and the 2,4,4'-trichloro-2'-hydroxydiphenyl compound is incorporated into at least some of the acrylic fibers. In another embodiment, the microbe-inhibiting agent or property is applied to the fibers which form either the outer casing or the filling for the article. In another embodiment, the microbe-inhibiting agent or property is bonded to at least a portion of the fibers. In a preferred embodiment of the invention, the microbe-inhibiting agent or property exhibits a zone of influence which extends beyond the portion of the fibers on which the microbe-inhibiting agent or property is incorporated.

The microbe-inhibiting agent or property can be applied to the outer casing. In one embodiment, the outer casing of the article comprises a tightly-woven fabric which prevents the passage of microbes therethrough. In another embodiment, the outer casing comprises a laminate, the inner layer of which has microbe-inhibiting or microbe-cidal properties.

The article according to the invention can have odor-controlling agents in the form of an odor-masking, odor-modifying and an odor-absorbing agent. The article can further include noise-making articles and the article can be washable. Further, at least one of the outer casing and inner filling can be impregnated with a flame-resistant modacrylic polymer.

According to one embodiment of the invention, the amount of microbe-inhibiting agent which is added to the article is computed in accordance with the following formula:

$$C_B = C_{MI} f_{MI}$$

wherein $C_B$ is the concentration of the microbe-inhibiting agent in the entire blend if the agent were to diffuse and become completely homogeneous throughout the blend. $C_{MI}$ is the average concentration of the microbe-inhibiting agent within the initially microbe-inhibiting fiber and $f_{MI}$ is the fraction of the filter blend that is composed of initially microbe-inhibiting fibers.

Further according to the invention, an amusement article for a domestic animal comprises a unitary piece of non-woven material defining the shape in the form of a small article which can be carried by a domestic animal and a microbe-inhibiting agent is applied to at least a portion of the unitary piece of material. The article is preferably in the form of an animal, a bone, a heart or a geometric shape. The non-woven material preferably comprises a fibrous batting selected from the group consisting of polyolefin, acrylic, nylon, polyester, polyurethane, polyethylene terephthalate, cellulose acetate, triacetate resin fibers and blends thereof and the microbe-inhibiting agent is applied to at least a portion of the fibers in the fibrous batting.

Still further according to the invention, a textile-based amusement article for a domestic animal comprises an outer textile casing formed of a tough, chew-resistant material defining a shape in the form of a small article of a size which can be carried by a domestic animal that comprises a high-pile component attached to a backing material to form an artificial fleece. The material is made in two layers which are sewn together at the edges with the high-pile component facing outwardly. A microbe-cidal agent is applied to the textile casing in an effective amount. The agent can be selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, polysubstituted imine salts and phosphate esters, and mixtures thereof.

Further according to the invention, there is provided a method for inhibiting the growth and presence of microbes on a pet article which can be carried by a domestic animal wherein the pet article has an outer textile casing defining the shape of the form of the article and preferably has an inner filling, the method comprising the step of providing at least one of the outer textile casing and the inner filling with an effective microbe-inhibiting agent or property. The microbe-inhibiting agent or property can be applied to the outer casing or to the inner filling, if any. The outer casing can be a woven, non-woven or knit fabric and the microbe-inhibiting agent or property is in the form of an anti-microbial agent which is applied to the casing or incorporated into the fibrous content of the textile fabric. Alternatively, the microbe-inhibiting agent or property can be a tightly-woven fabric for the casing which impedes the passage of microbes therethrough. Further, the micro-inhibiting agent or property can be a compound which is incorporated into any fibrous filling or applied to a portion of any fibrous filling.

In yet another embodiment of the invention, the outer casing can comprise a laminate of an outer textile fabric and an inner backing layer and the microbe-inhibiting agent or property can comprise a microbe-inhibiting or microbe-cidal property inner layer of the outer casing.

Microbe-inhibiting articles offer many advantages over the pet articles of the prior art. One advantage is that microbe-inhibiting articles inhibit the growth and proliferation of microbes; and, because microbial growth can create an environment that is attractive for many pests, such articles will inhibit the proliferation of pests as well.

The present invention can, therefore, provide a healthier environment for the pets and their "families" and, in turn, diminish the potential for illnesses, allergic reactions, and general discomfort. The microbe-inhibiting nature of the articles can also inhibit the emission of odors. This, in conjunction with the optional incorporation of an independent anti-odor activity into the articles, can allow the articles to possess a pleasant or neutral scent.

The useful life of articles made in accordance with the invention is prolonged for at least two reasons. First, because the articles will be cleaner and safer, one can comfortably use them for longer periods of time. Second, because microbes and pests can contribute strongly to the physical and chemical degradation of many materials, the articles of A textile-based amusement article can possess inherently longer useful lifetimes.

In addition to being safer, having a more pleasant scent, and possessing longer useful lifetimes, the articles of the present invention are more convenient due to fewer washings than articles of the prior art. In addition, by reducing the potential for undesirable microbes to enter into the mouth of the animal, the likelihood of "bad breath" will be reduced.

BRIEF DESCRIPTION OF THE DRAWINGS

The invention will now be described with reference to the drawings wherein.

DETAILED DESCRIPTION OF THE PREFERRED EMBODIMENTS

Figure 1:
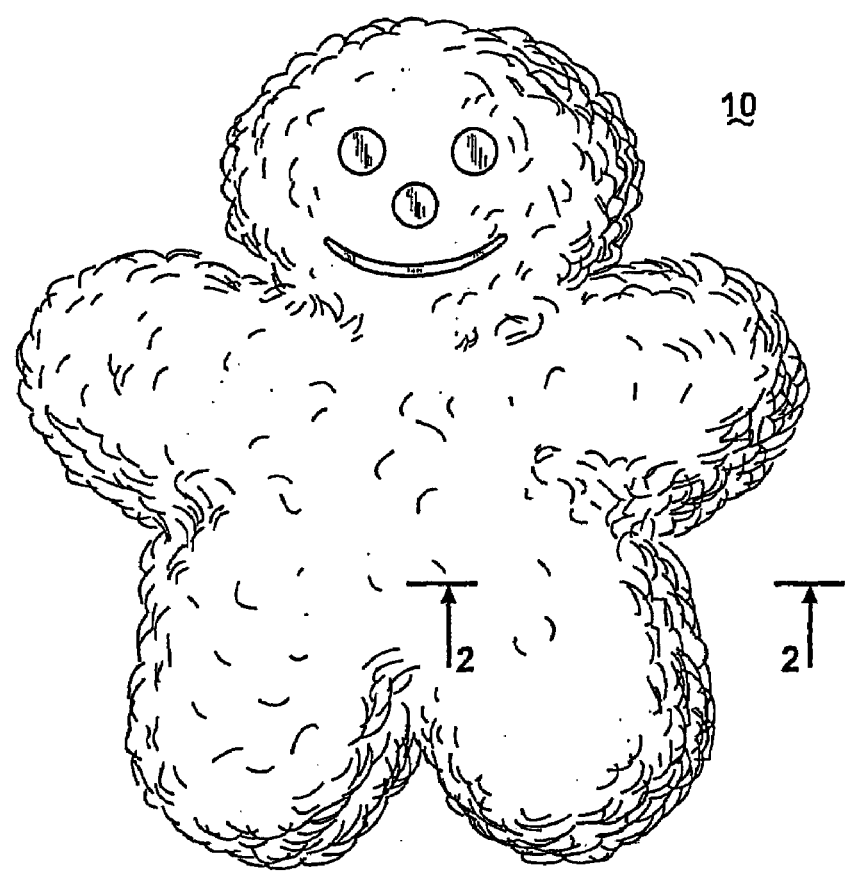
FIG. 1 is a perspective view of an amusement article in accordance with the present invention.

Referring now to the drawings and to FIG. 1 in particular, a first embodiment of an amusement article 10 is shown as having a bear-like peripheral geometry. The amusement article 10 preferably weighs less 250 grams and has a size in the range of 0.5–4 inches. While the amusement article 10 has been shown, for illustrative purposes only, as substantially bear-like any one of a number of periphal geometries are likewise contemplated for use including, but by no means limited to a human, ball, bone, lion, duck, bunny, cow, pig, lamb, dinosaur, monkey, elephant, koala, leopard, tiger, fish, footbal, penguin, and a whale. The only limitation with regard to the peripheral geometry of the amusement article 10 is that it must be configured such that an ordinary domestic animal can carry or otherwise play with the article.

Figure 2:
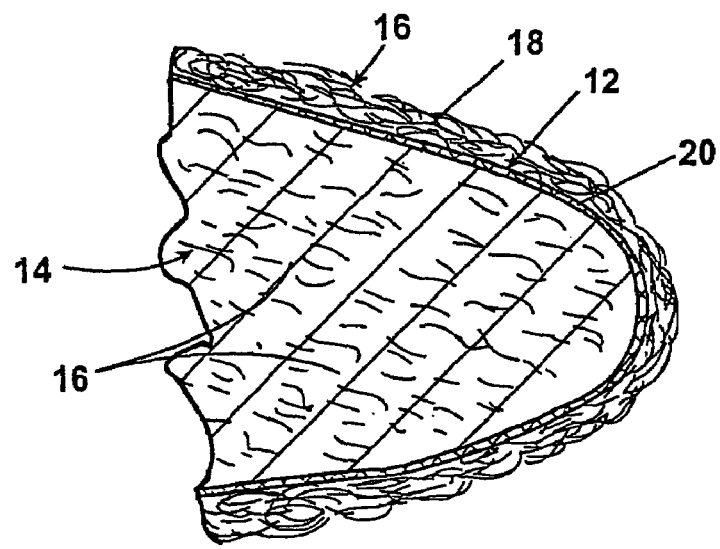
FIG. 2 is a cross sectional view of an amusement article in accordance with the present invention.

As shown in FIG. 2, the amusement article 10 generally comprises an outer casing 12, an inner filling 14, and a microbe-inhibiting agent or property 16. The outer casing 12 can be fabricated from woven, non-woven or knitted fabrics. Preferably the outer textile casing 12 is fabricated from a woven or knit fabric comprising a high pile component 18 that is attached to a backing material 20 and, in turn, forms an artificial fleece. In one embodiment, the outer textile casing 12 is made from a tightly woven fabric. Other material, such as rope, rubber balls, hard plastic components, etc., can be combined with the fiber-based outer casing to make a toy more attractive to a domestic pet. Other components can be included, e.g., to impart flame resistance to the amusement article 10. Modacrylic polymers of particular utility in the present context are those comprising acrylonitrile, vinylidene chloride, and/or vinyl bromide units.

The term "microbe-inhibiting" in the present invention subsumes all characteristics (and the means for imparting these characteristics) that cause a pet amusement article or toy to be inhospitable to microbes. In the invention, distinctions are made between three types of microbe inhibition: 1) microbe-cidal, 2) microbe-starving, and 3) microbe-impenetrable.

Microbe-cidal refers to a property whereby microbes are actively killed or otherwise rendered ineffective. If a microbe comes within a sufficiently close range (direct contact, for some materials; within a "zone of inhibition" for others) of a microbe-cidal material, it will be killed or otherwise rendered ineffective. Microbe-cidal properties can be imparted to materials by a variety of means. A preferred means uses microbe-cidal agents during the manufacturing process of the materials and/or treats the materials with microbe-cidal agents. A number of preferred agents are disclosed below. For the microbe-cidal property to be durable, it is often preferred that the agents be bonded in some manner to the materials comprising the pet article. Such materials exhibit smaller zones of inhibition than materials containing non- or weakly-bonded agents, but the microbe-cidal property with regard to microbes coming directly into contact with the material can be more durable. Using agents which are insoluble or only sparingly soluble in water can also be a key element for durability. As will be seen below, the present invention includes novel considerations involving the bonding of the microbe-cidal agents and their relations to the designs of the pet article.

Microbe-starving refers to a property whereby microbes are controlled or eliminated by deprivation of sources of nutrition. A material is said possess microbe-starving properties if microbes in contact with the material have difficulty acquiring the resources they need to survive. One can often provide or enhance a microbe-starving characteristic to a material by changing or altogether eliminating additives to the materials (e.g., plasticizers, fillers, or processing aids). Because adhered dust or liquids can provide nutrition for microbes, it is preferred that the material be provided with anti-adhesion properties (e.g., anti-static, low surface energy, etc.).

Microbe-impenetrable refers to the property of a material or coating whereby a microbe cannot pass through the material or coating. In this case, microbes may proliferate to some degree on a surface of the material, but such proliferation will be confined to the surface. Thus if an article is treated on its exterior by a microbe-impenetrable coating, microbes from the environment will not be able to pass into the interior of the article, will be limited in the degree to which they can proliferate, and can more readily be removed by washing. Appropriate placement of microbe-impenetrable materials is important to their effectiveness in providing the microbe-inhibiting property.

It is often prudent to fight the battle against microbial proliferation on several fronts. Thus, preferred microbe-inhibiting pet articles will often possess combinations of microbe-inhibiting behavior. For example, when a particular component of a pet toy is most susceptible to microbial attack, this component can be treated with both a microbe-impenetrable layer and a microbe-cidal agent, while the remainder of the article is treated with only the microbe-cidal agent. Further, an additive that serves as a resource for microbial growth may be important only for certain parts of the article. For example, plasticizers often act as an effective resource for microbial proliferation; and one can use the plasticizer only where the flexibility is needed, and then treat this area with an effective combination of microbe-inhibiting characteristics; and the remainder of the article, where the plasticizer was not used, may be less vigorously protected.

Physical cleaning can contribute to inhibiting the proliferation of microbes. Organic and inorganic material can act as a barrier between a microbe-inhibiting agent and the unwanted microbes (see, e.g., "*The Practical Application of Disinfection and Sterilization in Health Care Facilities*," by J. C. Cokendolpher and J. F. Haukos, American Hospital Association, Chicago, Ill., 1996). The microbe-inhibiting properties will therefore frequently be more potent if the article is clean. In addition, many organic materials can provide resources for unwanted microbes. Articles that possess microbe-inhibiting properties and are washable are therefore generally preferred; and articles which are less likely to accumulate organic or inorganic material, due to their structural design or to the materials used, are also preferred.

For durability, the microbe-inhibiting agents should be insoluble or sparingly soluble in the fluids with which they come into contact. This includes fluids associated with their use (saliva, urine, or other bodily fluids) as well as washing and cleaning fluids (the microbe-inhibiting activity should be durable to repeated home laundering). The insolubility may be an intrinsic characteristic of the agent-fluid combination, or it may be due to the fact that the agents are strongly bonded to the materials comprising the article. Both types are included in the present invention.

Although both water-durable and non-water-durable microbe-inhibiting components can be used with effectiveness in the present invention, if a non-water-durable microbe-inhibiting component is used, the exterior of the exposed material should desirably be provided with water-repellent or otherwise water-insulating qualities.

In a preferred class of embodiments, microbe-inhibiting properties are conferred upon one or more of the materials comprising the pet article by treating the material with or otherwise incorporating into the material a microbe-inhibiting agent. This microbe-inhibiting agent is a chemical species or particle which imparts to the material an effective microbe-inhibiting property. The microbe-inhibiting agents will often function primarily through a microbe-cidal mechanism. The microbe-inhibiting agents are typically chemicals, polymers, solutions (solid or liquid), or particulates (which may possess their own microbe-inhibiting activity or may act as hosts for other microbe-inhibiting agents). These microbe-inhibiting agents can exist in a variety of forms and be held in a variety of hosts before being incorporated into the pet article. For example, they can be dissolved in a liquid; they can be incorporated in or comprise the totality of a particulate phase, either dry or suspended in a liquid; they can be included within a plasticizer compound; or they can be pre-incorporated into a material used in manufacturing the article (e.g., one can employ materials which already possess microbe-inhibiting properties).

A good review of chemical microbe-inhibiting agents for use in polymers can be found in *Plastics Additives and Modifiers Handbook*, pp. 338–350, J. Edenbaum, Ed., Chapman and Hall, Great Britain, 1996.

The microbe-inhibiting treatment can be carried out at different points during the process of manufacturing the article or its component materials. For example, one can incorporate microbe-inhibiting agents in the fibers as they are being manufactured, which microbe-inhibiting fibers can be used as the filling of stuffed toys or as the fabric used as the external covers of stuffed toys. One can also manufacture a microbe-inhibiting rubber-like material for use in a component of the toy that is comprised of (e.g., molded) plastic. One can also treat (as by spraying or dipping) some or all of the materials after they are partially or completely manufactured (e.g., one can treat the external cover and/or the filling or some component of the filling of a stuffed toy article before its final assembly). Alternatively or in addition, one can treat (as by spraying or dipping) the pet article when it is finished or nearly finished in its manufacture.

Incorporation of microbe-inhibiting agents into the filler material of a pet article can be performed in several ways. They can be blended with the filling material such that the agent is dispersed throughout the packed filler (e.g., add a liquid containing the agent to a vat containing the filler material). In this case, depending upon the nature of the filling material, the agent used, and the presence or absence of other compounds (e.g., adhesion promoters, surfactants), the agent can adhere to the filler material and/or the material which confines the filler material; or the agent can remain detached from the filling material or the confining material. The filler material can optionally be treated with chemical agents so that the microbe-inhibiting agents become complexed with all of or part of the filler.

Including the microbe-inhibiting agents within the filler material itself (in intrafiber or intrafoam locations) generally provides greater durability. Intrafiber placement of the agents can be accomplished, inter alia, by known commercial fiber manufacturing techniques.

Some microbe-cidal agents must be in solution to work effectively, while others can be effective in a "raw" state in which they contact directly the microbes. When durability is a dominant concern, the latter are generally preferred; but the former can be used to construct pet articles in which contact with liquid (as saliva or urine) activates the microbe-cidal properties of the article.

In cases where surface attachment is desired, the use of adhesion promoters is preferred, particularly in conjunction with "raw" microbe-inhibiting agents, i.e., those which do not need to be in solution to work effectively.

When surface attachment to the cover of an amusement article is desired, it is often preferred to use a microbe-cidal/adhesion promoter to bond the microbe-cidal functionality to the cover. It is preferable to bond the agent to both the outer and inner surfaces of the cover; but bonding to only one surface (preferably the outer surface) is often sufficient.

When surface attachment to the filler of an amusement article is desired, it is often preferred to use a microbe-cidal/adhesion promoter to bond the microbe-cidal functionality to the filler.

In cases where a bonding agent is not used to attach the microbe-cidal functionality to the material of interest, or where such bonding is not entirely effective, it is often useful to diminish the rate at which the active microbe-inhibiting agent becomes de-activated. This can be done by inhibiting volatilization or adding stabilizers.

When the microbe-cidal agents are not bonded or are only weakly bonded to materials comprising the amusement article, it is preferred to package the articles such that the effective shelf-life of the antimicrobial character is enhanced. For example, when volatilization of the microbe-inhibiting agent or property is a problem, the packaging material can be made impervious to the volatilizing material.

It is useful to have a microbe-inhibiting agent at the surface of the amusement article, as well as in the interior. The microbe-inhibiting agent at the surface can be effective in inhibiting the proliferation of microbes directly on the surface. If suitable microbe-inhibiting agents are present in the interior, they can migrate to the surface as the agent initially at the surface becomes displaced. This process effectively constitutes a "time-release" of microbe-inhibiting agent. In this manner, the concentration of the agent can be maintained at a safe level, any odors associated with unduly high concentrations of the agent are avoided, and the period of effective microbe-inhibiting protection can be considerably prolonged.

The microbe-inhibiting agent can be applied in a liquid form (as dissolved in a solvent) and deposited on the surface of the cover or fiber material. By choosing properly the liquid and material, and optionally any additives, the agent can be made to penetrate the material; and a "time-release" system can be obtained.

A "time-release" property can also be provided by incorporating the active agent in a separate material, optionally particulate, which releases the agent in a time-controlled manner. For example, one can saturate a particulate zeolitic material with a microbe-inhibiting agent and incorporate the zeolitic material into the pet article. Alternatively, one can use a textile chosen specifically for its time-release characteristics for a particular microbe-inhibiting agent; and this textile can be incorporated in the article. Many other means for providing an effective "time-release" behavior with regard to microbe-inhibiting activity are possible under the present invention. In these cases, the microbe-inhibiting agent will generally function in a microbe-cidal manner.

There are many ways of applying a microbe-inhibiting agent to a piece of material used in an amusement article for a pet. For example, the material can be dipped or passed through a bath of a slurry containing the microbe-inhibiting agent. The material can then be passed through a pair of opposed rollers which control the amount of the slurry mixture retained by the material by controlling the pressure applied to the material as it is passed between the rollers. Upon leaving the squeeze rollers, the material is dried in a process oven. After drying, the material can be further processed by being coiled into rolls and/or cut into the final desired shape and size.

If some form of heat-assisted disinfection of the articles is desired, it is important to use material-agent systems which do not degrade in the disinfection environment (e.g., dishwashers, microwave ovens, conventional ovens, etc.). The softening or decomposition temperatures of the polymers and chemical agents used, for example, must be higher than the disinfection temperature used.

Because the accumulation of undesired organic or inorganic matter may reduce the efficacy of microbe-inhibiting protection, the articles can be designed with materials that reduce the tendency for such accumulation. This result can be accomplished by using low surface energy materials or applying a low surface energy coating; and/or by using anti-static materials or applying an anti-static coating. Non-hydrophilic materials (materials upon which water droplets form contact angles greater than about 30 degrees) are generally preferred to prevent the adhesion of such undesired matter.

It is often preferred to provide some surfaces of the pet article with both microbe-cidal and anti-adhesion properties. Thus, organic or inorganic matter is less likely to become attached to the article; if such matter does become attached, it is more easily removed; microbes are less likely to attach to or penetrate into the article; and microbes that remain in contact with the surfaces can be eradicated by the microbe-cidal properties of the surfaces. A preferred means of obtaining such a surface is to treat the surface with a combination of a microbe-cidal agent and a low surface energy agent (e.g., a group containing a fluorinated functionality). Both of these agents can be provided with an adhesion promoter functionality as well.

The anti-stick efficiency can be increased by including an anti-static agent, preferably an anti-static agent that can be bonded using an adhesion promoter, as a silane coupling agent.

Pets, especially dogs, often tear or otherwise damage the amusement articles that they use; and they sometimes eat the articles or their components. It is therefore important that the materials are non-toxic and non-carcinogenic at the levels used in the articles. Some agents are non-toxic even at relatively high concentrations (e.g., Triclosan, stabilized chlorine dioxide); other agents are non-toxic at relatively low concentrations, but become toxic at high concentrations (e.g., many unbonded quaternary ammonium compounds). If a pet article employs a time release property, one must ensure that the time-releasing materials do not contain concentrations of the agents that exceed that can be safely eaten by the animal of interest. Essentially, the pet should be able to eat the article without harm. Also, the treated materials should be non-skin-sensitizing, i.e., should not generally cause allergic or other undesirable reactions on the skin or other membranes of the pet or people who effectively come into contact with the materials.

For safety, durability, microbe-inhibiting efficacy, and ease of use, phenol derivatives, especially 2,4,4'-trichloro-2'-hydroxydiphenol (sometimes known, among other names, as Triclosan, Irgasan, or Microban) incorporated into the constituent materials (e.g., fibers or foam) at the time of manufacture of such materials are particularly preferred. This provides most readily for the microbe-inhibiting agent to become an integral part of the material. These agents in particular can be readily incorporated in the manufacturing processes for the constituent materials; they are generally non-toxic and non-carcinogenic (even at relatively high levels); they generally do not cause adverse skin reactions; they tend to migrate from the bulk of the material to its surface when they are depleted from the surface; and they are very efficacious in inhibiting the proliferation of a wide variety of microbes.

Filling Materials

The inner filling 14 can be fabricated from a fibrous filling, foam, or beads. Preferably the fibrous filling is fabricated from polyolefin, acrlyic, nylon, polyester, polyurethane, polyethylene terephthalate, cellusoe acetate, and triaceate resin fibers. Mixtures of any and/or all of the resin fibers are likewise suitable for use in the amusement article 10. When beads are used as the inner filling a mesh bag can be used to retain the beads in the event that the outer casing would open. While the beads can be fabricated from any one of a number of compositions, polystyrene is the preferred composition due to, among other things, cost and weight factors.

When the inner filler 14 is fabricated from polyolefin resins, polyethylene and polypropylene are preferabe—especially low-density polyethylene resins such as Dow Chemical's "LDPE 640."

When acrylic polymers are used as the inner filler 14, acrylonitrile units and either vinyl acetate, methacrylate or methyl methacrylate units are preferred.

The inner filling 14 can also be fabricated from foam, due to their ease of manufacture and their low cost on a volume basis. Foam materials can be cut to the desired shape and then employed as a filler within a pet article; they can also serve as the article itself; or the foam can be formed within a cover material for the article. If a cover material is used, it is preferred to form a contained structure with the cover material (effectively a shaped "bag") and then to inject microbe-cidal foam precursors through an aperture in the structure and foam in place. The aperture can then be sealed.

Cover and Lining Materials

Various materials in sheet form can be useful in the construction of microbe-inhibiting amusement articles for pets, either as the cover or containment structure of the article or as a microbe-inhibiting lining that can be incorporated into a conventional pet article to provide microbe-inhibiting properties. For example, one can attach such a material to the inner side of the cover of a stuffed pet toy. In using such linings, it is generally preferred to employ materials with low permeability (e.g., microbe-inhibiting vinyl sheets); but when sewing is necessary, conventional fabrics (e.g., microbe-cidally treated cotton or poly/cotton blends) are preferred for ease of manufacturing of the article.

The design of an attractive microbe-inhibiting article for pets involves a unique balance of considerations with regard to material selection. The demands placed on the efficacy of the microbe-inhibiting agents used are lessened by using materials that are naturally less inclined to harbor microbial proliferation. The natural microbial resistance of materials derived from cotton, flax (linen), and rayon fibers are particularly poor. Materials derived from acrylic, polyester, nylon, olefin, triacetate, rubber, and spandex fibers possess much better natural microbial resistance.

Because microbial proliferation usually requires the presence of moisture, it is additionally attractive that the constituent materials do not readily take-up or absorb/adsorb water. The degree to which fibers do take-up or absorb/adsorb water is a function of the surface properties and the microstructure (e.g., porosity). One is generally interested in fibers that are poorly wetted by water and display a low moisture regain. Polyester and acrylic are two of the most useful, commercially available fibers in this regard. Because they both also possess good natural microbial resistance and readily take-up microbe-inhibiting chemicals, they are preferred materials from which to construct microbe-inhibiting amusement articles for pets.

Nylon possesses good natural microbial resistance, and is thus attractive for use. Acetate possesses only moderate natural microbial protection (triacetate is better); and if used to a significant extent, it should be incorporated with a microbe-inhibiting agent.

Another consideration which is relevant for dog toys relates to the observation that dogs often prefer toys that pick up their scents; and this is encouraged on toys that can absorb or otherwise take up some of the dog's saliva. It is therefore sometimes advantageous to include some fraction of material that is hydrophilic or at least not strongly hydrophobic, and which displays a moderate moisture regain. For example, one can include a fraction of cotton or acetate (or triacetete) fiber.

A preferred article is thus manufactured using materials derived from acrylic, polyester, and/or nylon fibers; and smaller parts of cotton and/or acetate (or triacetate) fibers can be incorporated advantageously as well. Some fraction of these materials in the preferred article are incorporated with microbe-inhibiting agents such as 2,4,4'-trichloro-2'-hydroxydiphenol (e.g., Triclosan) at the time of manufacture of the constituent fibers.

Selection of Plasticizer

Although some polymers possess a significant degree of natural inhospitableness to microbial proliferation, they can lose this desirable property if they are processed using certain plasticizers. The plasticizers used in processing many polymers are digestible and/or degradable by microbes. If a plasticizer is to be used in processing materials used for constructing an amusement article for a pet, it is preferred to chose a plasticizer that does not diminish the natural microbe-inhibiting property of the polymer. Listed below are plasticizers that are resistant to fungal growth: Abietic acid; hydrog. methyl abietate; tri-n-butyl aconitate; triethyl aconitate; di-(2-ethylhexyl)adipate; di-(2-ethylhexyl)acetate; ethyl-o-benzyl benzoate; chlorinated diphenyls; chlorinated paraffins; tri-n-butyl citrate; triethyl citrate; 2-nitro-2 methyl-1,3-propanediol diacetate; dimethyl phthalate; di-n-propyl phthalate; diisopropyl phthalate; dibutyl phthalate; diisobutyl phthalate; diisodecyl phthalate; dihexyl phthalate; dicapryl phthalate; di-(2 ethylhexel) phthalate; di-(2 ethylhexyl) phthalate; dicyclohexyl phthalate; dicyclohexyl phthalate; and dibenzyl phthalate.

Non-Wovens Some articles of the invention can be made in whole or in part from non-woven fabrics. These are generally made from extruded continuous filaments or from fiber webs or batts strengthened by some form of bonding between or among fibers. The fibers can be bonded, e.g., by heating (including use of low-melting coatings), by adhesives, stitch-bonding or mechanical interlocking (e.g., needling).

A preferred base material is often polyester or olefin fibers or filaments; and preferred non-woven for the present invention is a very high-loft, low density type such as those used in filtration systems. These non-wovens can be prepared at large thickness (on the order of inches) and die-cut into toy shapes.

More traditional non-woven fabrics (e.g., non-woven felt) can be used as cover materials in articles of the present invention.

In preparing microbe-inhibiting fibers, the microbe-inhibiting agents can be incorporated in a variety of ways, including adding the microbe-inhibiting agents to the melt or the spin dope from which the fibers are spun; or impregnating or otherwise treating the filaments as they are being stretched, washed, dried, cooled, solidified, or otherwise treated. One can also treat finished fibers by soaking or spraying in a solution containing a microbe-inhibiting agent.

When synthetic fibers are being used, it is preferred to add the microbe-inhibiting agents to the melt or the spin dope from which the fibers are spun (extruded). In this case the microbe-inhibiting agent becomes an integral part of the fiber; and the durability of the resulting microbe-inhibiting efficacy is generally enhanced considerably. Phenol derivatives, especially 2,4,4'-trichloro-2'-hydroxydiphenol (sometimes known as Triclosan, Irgasan, Microban, or by other names) are particularly attractive. Organotins, especially Tri-n-butyltin maleate (as in Ultra Fresh DM-50), are also attractive.

In the case of fibers that are melt spun, it is important to ensure that the degradation temperature of the microbe-inhibiting agent is higher than the melt temperature. Because of the lower temperatures used, solution spinning methods are generally preferred for the manufacture of microbe-inhibiting fibers.

If the microbe-inhibiting agent is to be incorporated into a preformed fiber or tow, it is often preferred to do so when the fiber still possesses an open and/or porous structure. This particularly beneficial when solution-spinning acrylic or modacrylic fibers, where the microbe-inhibiting agent can be applied to the filaments from the finish bath through which the filaments pass en route to the drying rolls. When the filaments are then processed on the drying rolls, the microbe-inhibiting agent is retained in the fiber. After the microbe-inhibiting agent is applied to the tow, care must be taken so that the microbe-inhibiting agents are not volatilized during subsequent processing.

In the case of melt-spun fibers, the microbe-inhibiting agents can be applied to the filaments either prior to or along with the spin finish application. When applied prior to the spin finish application, the microbe-inhibiting agents are preferably are applied from an aqueous solution or emulsion thereof. A spin finish-containing agent can be applied to the filaments in a conventional manner, e.g., by passing the filaments over a metered finish applicator where a predetermined amount of finish is applied to the filaments.

Fiber to be used as fiberfill can also be treated so as to possess microbe-inhibiting properties at the time it is incorporated into the containment structure by a blowing/filling machine. The blowing/filling machine can be constructed so as to spray, soak, or otherwise contact the fiber with the appropriate microbe-inhibiting treatment solution. For this application, Tri-n-butyltin maleate (Ultra Fresh DM-50) is a preferred agent.

It is important to note that post-treatment methods involve importantly different considerations when one is using a "strongly-bonded" type of agent. In the "diffusing" or "non-strongly-bonded" case, one immerses or otherwise exposes the materials to a solution containing a particular concentration of the agent. Generally, the agent diffuses into the material until its concentration in the material is comparable to the concentration in the solution, i.e., the treatment level of the material is essentially proportional to the concentration of the agent in solution; and the agent concentration in the solution is the primary controlling variable. In typical treatments, the agent in solution is not appreciably depleted; and the amount of material exposed to the treatment solution is not carefully monitored and is not considered a primary variable of the treatment process.

In the strongly-bonded case, however, the agent usually does not diffuse into the material (fiber, fabric, etc.); rather, it chemically reacts with the surface of the material. Here one attempts to arrange conditions such that most of the "reactable" agent present in the solution reacts with and bonds to the surface of the material being treated. Knowledge of the amount of material being treated is thus important in determining the treatment level; and the material amount, along with the agent concentration in solution, are considered controlling variables of the treatment.

As used herein, the "amount of material," means the "amount of reactable surface" of the material. For porous materials that can take up the solvent in their interiors (e.g., many fibers or fabrics), the mass of the material is often used as an indicator of the reactable surface area—i.e., one can specify an agent level in solution per unit weight of material being treated. For non-porous materials and/or materials which do not absorb the solvent being used (hard plastics, highly solvent-phobic materials), more direct knowledge of the reactable surface area is needed. The length of the cut fiber figures importantly in the blending process. It the fibers are too long, blending can be ineffective. If the microbe-inhibiting fiber is not homogeneously blended, the microbe-inhibiting resulting efficacy of the resulting amusement article can be dramatically reduced: Filling using a blowing/filling machine can also become problematic with longer fibers (if the fibers are very long, hand filling can also be considerably more difficult). For articles of the present invention, the cut length of the fiber should be between 0.1 and 8 inches, preferably between 0.3 and 5 inches, and most preferably between 0.4 and 3.5 inches.

When fiber blends are used, it is preferred that both the microbe-inhibiting fiber and the non-microbe-inhibiting fiber both possess the same cut length.

Microbe-inhibiting fabrics may be constructed by weaving, knitting, or otherwise forming the fabric from fibers which possess the desired microbe-inhibiting properties. Alternatively, the fabrics can be post treated via spray-treating or by using a padding system such as are common in the art of textile finishing. For post treatment, Tri-n-butyltin maleate (as in Ultra Fresh DM-50) is a preferred diffusing microbe-inhibiting agent (at fabric pick-up about 0.1%–0.5%); and 3-trimethoxysilylpropyldimethyloctadecyl ammonium chloride (as in Dow Corning 5700) is a preferred strongly bonded microbe-inhibiting agent (at fabric pick-up about 0.08%–0.15%).

The preferred means for obtaining microbe-inhibiting foams is to include a microbe-inhibiting agent in the formulation of one of the foam precursors (i.e., before the material is foamed) A preferred microbe-inhibiting foam is obtained by adding Ultra Fresh DM-50 to the polyurethane foam formulation before foaming (typically in amounts ranging from 0.04% to 0.6% relative to the total weight of the formulation). Another preferred means is to use Dow Corning 5701 (a reactive silane quaternary ammonium compound, which works much like Dow Corning 5700). This agent is also added into the formulation of the foam before foaming (typically in amounts ranging from 0.1% to 1.2% relative to the amount of polyol).

It would be a further benefit to articles of the present invention that they resist the proliferation of mites, fleas, ticks, and other pests. One means for inhibiting the ability of such pests to proliferate in the interior of the articles of the present invention is to use outer fabrics possessing very tight weaves (so the pests cannot pass through the interstices or pores of the fabric. Another means, particularly efficacious for inhibiting the proliferation of dust mites, is to use the microbe-inhibiting agent Ultra Fresh DM-50 in treating or preparing the fabric; foam, fiber and/or other materials used in the article (this agent appears to possess the ability to limit dust mites).

Microbe-Inhibiting Agents

A wide variety of chemicals can be used as microbe-inhibiting agents in the present invention. For listings of chemical additives which can impart anti-microbial properties, see the *Plastics Additives and Modifiers Handbook* pp. 338–350, J. Edenbaum, Ed., Chapman and Hall, Great Britain, 1996); *Plastics Handbook* (*Modern Plastics,*1994, McGraw Hill); and *The Practical Application of Disinfection and Sterilization in Health Care Facilities* (J. C. Cokendolpher and J. F. Haukos, American Hospital Association, Chicago, Ill., 1996).

Nearly all heavy metals possess some degree of microbe-inhibiting activity (especially of the anti-fungal kind). Copper naphthenate, e.g., can be applied from a solvent bath, optionally with additional microbe-inhibiting agents in the same bath. Alternatively, fabric or fill can be impregnated with a copper salt dissolved in ammonia, and then treated with napththenic acid. Other useful copper salts include hydroxynaphthenate, stearate, tallate, oleate, resinate, acrylate, furoate, antimonate, and chloracetate.

Chlorine dioxide, typically in aqueous solution, also possesses microbe-inhibiting properties, and it can be used to impart such properties to amusement articles for pets. The articles can be soaked in the solution or can be treated topically with the solution, or constituents of the articles can be treated with the solution. Chlorine dioxide is attractive because it can be obtained in a stabilized form in which it is non-toxic. It is used in toothpaste and mouthwash for humans, and it is a particularly preferred microbe-inhibiting agent or property for the invention.

The microbe-inhibiting properties of quaternary ammonium compounds are well known; and several examples are given below. They can be used alone or in conjunction with other microbe-inhibiting agents, preferably in conjunction with adhesion promoters, especially alkoxysilane coupling agents. A preferred example is Dow Corning 5700 microbe-inhibiting agent (3-trimethoxysilylpropyldimethyloctadecyl ammonium chloride). Additional agents suitable for use in this context include cetylbenzyldimethyl ammonium chloride, tertiary octylphenoxyethoxyethylbenztyldimethyl ammonium chloride, and lauryl pyridinium chloride.

Suitable other quaternary ammonium compounds include polyamniopropyl biguanide, 1-(3-chlorallyl)-3,5,7-triaza-1-azoniaadamantane chloride (available under the trade name Dowicil 200 from Dow Chemical). Still other suitable quaternary ammonium compounds are included in the next section.

Effective organic sulfur compounds include the microbe-inhibiting organic preservatives containing 3-isothiazolone groups and sodium pyrithone. Halogenated compounds suitable for use in the present context include 5-bromo-5-nitro-1,3-dioxane (available from Henkel under the trade name, Bronidox); 2-bromo-2-nitropropane-1,3-diol (available from Inolex under the trade name, Bronopol); 1,1'-hexamethylene bis 5-(p-chlorophenyl) biguanide (commonly known as chlorohexidine) and its salts; 1,1,1-trichloro-2-methylpropan-2-ol (commonly known as chlorobutanol);

4,4'-(trimethylenedioxy) bis-(3 bromobenzamidine) diidethionate or dibromopropamidine. The addition of thiazole derivatives, specifically 2-mercaptobenzothiazole, is useful. Thiazoles can be used effectively in mixed combination with other chemicals such as the quaternary ammonium salts and selected metal derivatives, e.g., of mercaptobenzothiazole, in which the metal itself possesses antimicrobial properties.

Suitable phenyl and phenoxy compounds include 4,4'-diamidino-alpha,omega-diphenoxypropane diisethionate (commonly known as propamidine isethionate); and 4,4'diamidino-alpha,omega-diphenoxyhexane diisethionate (commonly known as hexamidine isethionate. Other examples are benzyl alcohol 2-phenylethanol, and 2-phenoxyethanol.

Chlorinated phenolic compounds are generally preferred for incorporation into the bulk of many materials. 2,4,4'-trichloro-2'-hydroxydiphenol is especially attractive and, for reasons discussed herein, is a highly preferred agent in the present invention. Other possible chemical names for this agent are chloro-2-(2,4-dichlorophenoxy)phenol; 5-chloro-2-(2,4-dichlorophenoxy)phenol; or 2,4,4'-trichloro-2'-hydroxydiphenyl ether. Trade or common names which are comprised primarily of the agent are Triclosan, Irgasan, Irgasan DP-300, Microban, Microban B, Lexol 300, and others. The Ultra Fresh family of agents, solutions, and materials, available from Thomson Research Associates, often include significant amounts of this triclosan-type additive (sometimes, along with quaternary ammonium compounds and/or tributyltin oxide compounds).

DM-50 (Thomson Research Associates) is a preferred form of the preferred organotin agent, tri-n-butyltin maleate.

Another preferable microbe-inhibiting agent is known by the trade name Intersept. It is a complex of polysubstituted imine salts and trialkyl phosphate esters with free alkylated phosphoric acid. It is relatively non-toxic and has been used as an antimicrobial finish on many building materials.

A further preferred type of microbe-inhibiting agent is typified by the MicroFree brand of particulates (available from DuPont). These particulates generally comprise a core particle (zinc oxide, titanium oxide, or barium sulfate) over which is coated a microbe-inhibiting active layer (silver, copper oxide, and/or zinc silicate). A barrier layer (to control the rate of release of the active component) and a dispersion coating (to facilitate dispersion of the particles in host materials) are included on top of the active layer. The particles range from about 0.3 μm to 1 μm in size. They can be incorporated into many resin systems for plastics processing, into the dope before fiber spinning, and into many coating systems for post-treatment. Good microbe-inhibiting efficacy can be imparted to various materials using these particles, and the resulting materials are generally non-toxic, very stable, and cost effective.

The microbe-inhibiting agent chosen depends on many factors including toxicity, the desired method of incorporation, material compatibility issues, and economic considerations.

Lists of Compounds and Solutions with Selected Concentrations

Below is a listing of chemical compounds with demonstrated effectiveness for various microbe-inhibiting applications. The effectiveness of each depends upon its concentration, the presence and concentrations of other microbe-inhibiting agents, the nature of the surface, the temperature, the overall pH of the solution, etc.

Most of the microbe-cidal chemicals listed are followed by a representative effective concentration range. These concentration ranges are meant to be typical and representative; the concentration actually used can vary with other conditions of the treatment, with the nature of the host material, with the concentrations and efficacies of other microbe-cidal agents (or microbe-starving or microbe-inhibiting properties) present, and with the degree of toxicity allowable.

As used herein, all concentrations given in units of percent are understood to be weight percent (unless otherwise stated).

Chemical Compounds Commonly Used as Additives in Polymers

The agents listed in this section can be used as additives in polymers, but many can also be used effectively in liquid treatment solutions. The preferred concentrations depend on a variety of factors, including the type of polymer, its required physical and chemical properties, the degree of toxicity allowable, and the environment in which the pet article is to be used.

Unless otherwise stated, when concentrations are given below, they correspond to the percentage of the total plastic or liquid formulation that is the microbe-inhibiting agent. In some cases, a preferred material is given with which the additive is compatible and effective. The chemical compounds (and in some cases broad categories of compounds) and typical concentrations are as follows:

Copper-8-quinolinolate (0.2–4%, in, e.g., vinyl); mercaptan (0.2–4%, in, e.g., vinyl); tetramethylthiuram disulfide (0.4–4%, in, e.g., vinyl or cellulose nitrate); copper napthenate (0.2–4% in, e.g., PVC or PVA); pentachlorophenol (1–20%, in, e.g., lacquer or cellulose nitrate); phenyl mercuric formate (0.05–10%, in, e.g., nylon); pentachlorophenol (0.2–4%, in, e.g., celluose nitrate); 10,10'-oxybisphenoxarsine (OBPA) (0.005–2%, in a variety of plastics, including vinyl, PVC, and others; sometime sold under trade names, "Intercide" or Vinyzene); organotins (0.005–2%, in, e.g., PVC) (examples of organotins are, e.g., bis (tri-n-butyltin)sulfosalicylate (0.25–0.5% of plasticizer, used in e.g., PVC), or the preferred tri-n-butyltin maleate (0.005–1%, in, e.g., urethanes, paint-compounds); brominated salicylanilide (0.04–1%, in, e.g., polyethylene).

Phenolic species, particularly especially chlorinated phenolics (hexachlorophene, dichlorophene, p-chlorometacresol, p-chlorometaxylenol, o-benzyl parachlorophenol, and o-phenylphenol), and especially 2,4,4'-trichloro-2'-hydroxydiphenol (0.05–10%)—the latter has been incorporated successfully into a number of plastics and other products; it can be written as is 2,4,4'-trichloro-2'-hydroxydiphenol, or as 5-Chloro-2-(2,4-dichlorophenoxy) phenol; and may be referred under the names Triclosan, Irgasan, Microban, Microban B, Lexol 300; quarternary ammonium compounds (e.g., quarternary ammonium napthenate (0.5–6% of the plasticizer, used, e.g., in PVC); blends of substituted ammonium salts of alkylated phosphoric acids mixed with a free alkylated phosphoric acid (especially complexes of polysubstituted imine salts and trialkyl phosphate esters with free alkylated phosphoric acid)—0.1–4% of the coating used; Fungitrol 11 (N-trichloromethylthiopthalimide powder); Vancide 89 (N-(trichloromethylthio)-4-cyclohexene-1,2-dicarboximide, powder); Microchek 11 (2-N-octyl-4-isothiazlin-3-one, liquid); Omacide (zinc pyrithione); Preventol (N-(fluorodichloromethylthio)pthalamide); Apacider (silver hydroxyapatite); and Vinyzene SB-129 contains as an active ingredient N-(2-Methyl-1-naphthyl)maleimide.

Design of Microbe-Inhibiting Amusement Articles for Pets

Figure 3:
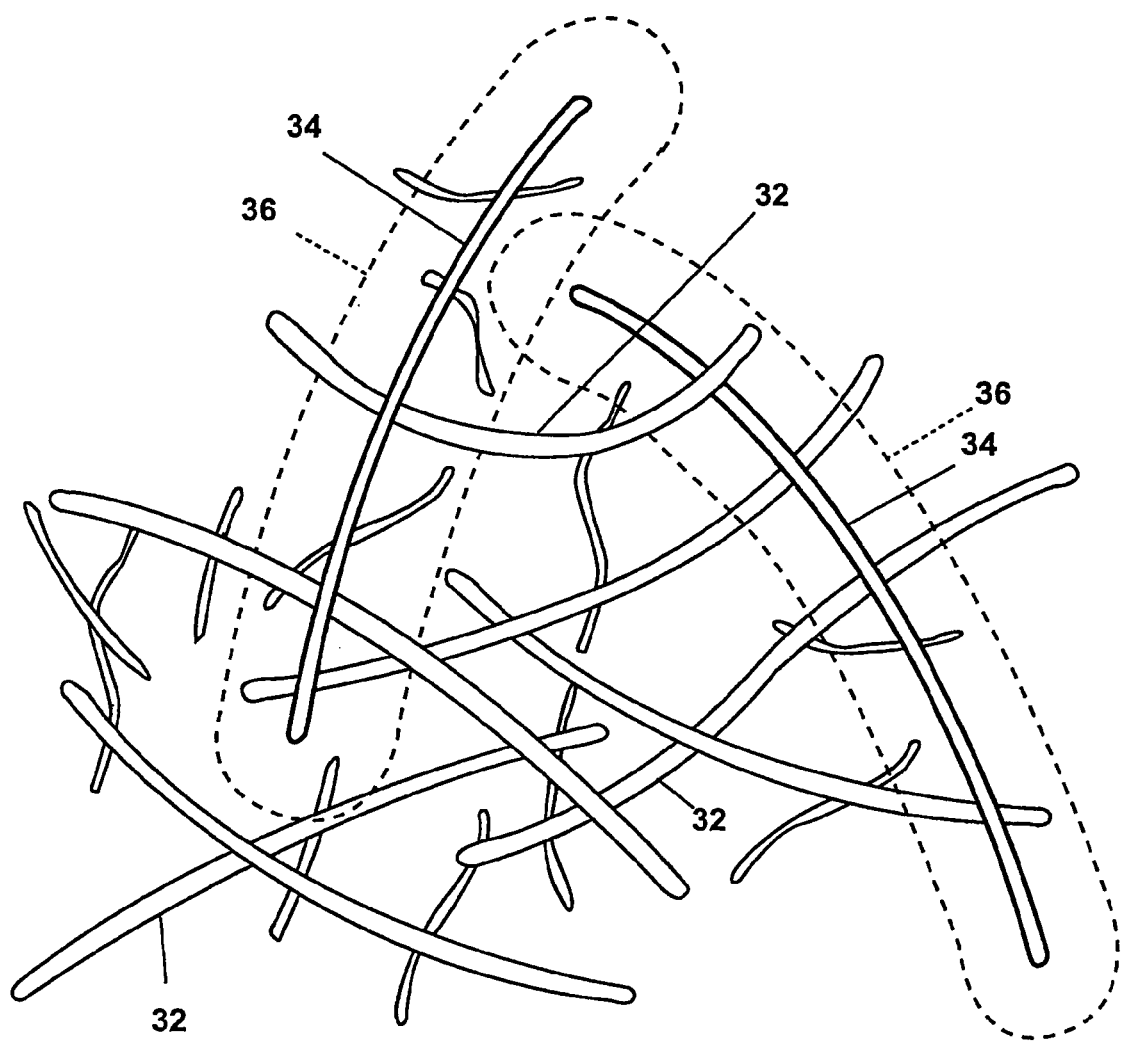
FIG. 3 is a perspective view of an inner filling of an amusement article in accordance with the present invention.

Some microbe-inhibiting materials contain an agent which can diffuse out of the material. Such materials generally exhibit a significant "zone of inhibition," whereby microbial growth is effectively inhibited some distance away from the material (e.g., see *Plastics Additives and Modifiers Handbook* pp. 338–350). In these materials, the agent is not fully bonded to or otherwise trapped in the material, and it can be transported from the material into its surroundings. FIG. 3 demonstrates the zone-of-inhibition, shown in dashed lines 36, as surrounding the microbe-inhibiting fibers 34, and encompassing regions containing the initially non-microbe-inhibiting fibers 32.

In other cases, the microbe-inhibiting agents may be strongly bonded to or otherwise trapped within the host material. The zone of inhibition is very small for these materials; and microbes are killed or otherwise inhibited only by coming into direct contact with the material.

The behavior of the zone-of-inhibition 36 affects the design of efficacious microbe-inhibiting amusement articles for pets. For example, if the fiber used as the filling of a stuffed pet article has been provided with a strongly bonded microbe-inhibiting agent, then the zone of inhibition is very small; and the filling should be composed almost exclusively of the microbe-inhibiting fiber. In addition, the microbe-inhibiting fiber will not spread its microbe-inhibiting efficacy to the cover; and if any protection is desired on the cover, it must be separately supplied.

If the fiber is provided with a diffusing microbe-inhibiting agent, however, the design is more complicated. It is preferred to use a fiber blend in which only a modest fraction of the fiber is provided with microbe-inhibiting properties. Over time, and accelerated by use, the agent will diffuse to the fibers which were not initially provided with microbe-inhibiting properties. In addition, if the agent is suitably mobile, it can impart a microbe-inhibiting characteristic to the cover as well. In this case, one must properly consider the interplay between the characteristics of the zone of inhibition (its extent, shape, decay characteristics, and dependence on the surrounding fiber packing density), the rate of depletion of the microbe-inhibiting agent from the fiber (and how this impacts the characteristics of the zone of inhibition), and the distribution of the microbe-inhibiting fiber within the total filler.

If the agents are extremely mobile and weakly attached to the host material, they will readily and rapidly diffuse to contiguous materials that contain smaller concentrations of the agents; and this will occur until the overall concentration approaches uniformity. In this instance, as long as there is extensive contact among the fibers comprising the filler, the zone of inhibition is essentially limitless in extent; and, for the pet article to be provided with microbe-inhibiting properties, one must only ensure that there is enough agent present in the fibers that initially contain the microbe-inhibiting agent that the overall concentration will remain at a sufficient microbe-inhibiting level for the desired lifetime of the article. Thus, the important parameter in designing articles in this case is the total concentration of the microbe-inhibiting agent. Issues related to the design of yarns and fabrics under these conditions are discussed in U.S. Pat. Nos. 3,959,556 and 4,842,932.

The prior art, however, provides no teaching for the case in which an effectively finite zone of inhibition is exhibited by the microbe-inhibiting fiber, nor for the case in which the microbe-inhibiting material is particulate in nature, nor for the case in which the fibers comprise the filling portion of a containment structure (rather than the filaments of a yarn or of a fabric). Teachings for these cases are provided below.

An important distinction between fiber as used as filling in the present invention, as opposed to fiber as used in yarns and fabrics of the prior art, is that the fiber used as filling in the invention is typically the component of the interior of a containment structure within which the great majority of the space (by volume) is typically comprised by air.

As mentioned above, the prior art deals with cases in which the diffusing microbe-inhibiting agent easily leaves its initial host and permeates the entire space of the yarn or fabric of which it is part (i.e., an effectively infinite zone-of-inhibition). In systems of this invention, however, there are typically restrictions on the transport of the microbe-inhibiting agents and/or the agents possess a significant degree of attachment to their hosts; and a finite zone-of-inhibition is present. In this case, for adequate microbe-inhibiting protection, one must ensure at the very least that that the microbe-inhibiting fibers and their associated zones of inhibition comprise a sufficient volume fraction of the containment volume.

In the invention, there are two basic approaches to the design of effective microbe-inhibiting pet amusement articles: 1) an empirical approach, in which key design variables are identified and appropriate ranges of and relationships among these variables are determined with respect to the effectiveness of the microbe-inhibiting character of the so-designed articles; and 2) a direct approach, in which the effective extent of the zone-of-inhibition is determined experimentally under conditions which simulate actual use of the article; and the appropriate ranges of and relationship among design variables are thereby calculated using a mathematical model.

One means for determining whether a given design displays the desired degree of microbe-inhibiting efficacy is as follows. Construct the amusement article according to the design; soak the article in a fluid containing microbes (e.g., tap water) for five minutes; transfer the article to the interior of an air-tight bag; heat at a desirable incubation temperature (e.g., 37° C.) for a desirable time (e.g., 8 days); and have another person open the bag and grade the severity of the odor on a scale of 1 (bad) to 3 (no odor). An effective design produces no noticeable odor.

It is necessary to determine several parameters of the components of the pet amusement article:

1. The volume of the cover or containment structure, $V_c$. This is the total volume that can be held within the cover or containment structure. This can be determined as follows: fill the cover with small plastic beads empty the beads into a large graduated cylinder or other container from which one can read the volume and read the volume.
2. The densities of the fibers. It is necessary to know the fiber densities so that one can calculate the fiber volume from the fiber mass. If a hollow fiber is being used, it is usually advisable to use the effective of average or density.
3. The radius of the fibers, $r_f$. The denier, which is the mass of a fiber divided by its length, can be used to estimate the effective fiber radii, $r_f$, as:

$$r_f = \sqrt{\frac{denier}{9\pi \cdot 10^5 \cdot \rho}}$$

where $\rho$ is the average density (in units of $gm/cm^3$) of the material comprising the fiber. If the fibers are roughly circular in cross section, $r_f$ should correspond closely to the average physical radius of the fibers. If the fibers are decidedly non-circular in cross-section, $r_f$ is an effective averaged radius (i.e., the relevant behavior is much as if the fibers were of circular cross-sectional radius, $r_f$). The use of the above becomes increasingly accurate for fibers which are more circular in cross-section and which possess a narrower distribution in cross-sectional size. If the fibers are hollow, the proper equation is somewhat more complicated; but one can calculate the radius using information supplied by the manufacturer.

After the above parameters are obtained, one can proceed to the design of the microbe-inhibiting article. There are several key variables that must be considered:
1. The volume fraction, $x_o$, of initially microbe-inhibiting fiber. This is equal to the total volume of initially microbe-inhibiting fiber, $VMI_o$, divided by the total volume of the containment structure, or $x_o$, $=VMI_o/V_c$
2. The average concentration of the microbe-inhibiting agent, $C_{MI}$, within the initially microbe-inhibiting fiber.
3. The fiber blend volume fraction, $\rho_B$. This is the volume fraction of a containment structure that is comprised of fiber of any kind.

Then the following calculations can be made:

1. The fraction of the fiber blend that is composed of initially microbe-inhibiting fiber, $f_{MI}$:

$$f_{MI} = \frac{x_0}{\rho_B} \quad (1)$$

2. $C_{MI}$ is used to calculate the average blend concentration, $C_B$, as $$C_B = C_{MI} f_{MI} \quad (2)$$

$C_B$ would be the concentration of the microbe-inhibiting agent in the entire blend if the agent were to diffuse and become completely homogeneous throughout the blend (i.e., it is the average concentration of the microbe-inhibiting agent throughout the blend). If protection throughout the fiber blend is to be obtained, this value must be above the minimum efficacy level (sometimes referred to as a "minimum inhibitory concentration) for the particular microbe-inhibiting agent used.

Empirical Method

In designing effective microbe-inhibiting articles using a filling, where the filling possesses microbe-inhibiting properties, the design parameters of the fill must be chosen properly. The three key design variables are $x_o$, $C_{MI}$, and $\rho_B$. The variables $x_o$ and $f_{MI}$ must be sufficiently large that the initially microbe-inhibiting fiber can "spread" its inhibitory qualities throughout at least a predominant fraction of the entire blend, and preferably to the cover material as well; but not so large that the cost becomes prohibitive. $C_{MI}$ must be sufficiently large that there is enough microbe-inhibiting agent in the initially microbe-inhibiting fibers to spread to the initially non-microbe-inhibiting fibers (and optionally to the cover material) and still maintain a concentration that exceeds the minimum inhibitory concentration. $\rho_B$ must be sufficiently large that the microbe-inhibiting efficacy can spread effectively throughout the article. If, for a given $x_o$ and $f_{MI}$, $\rho_B$ is too small, the fibers will not be intermingled sufficiently, and the agent will not be able to diffuse effectively. If $\rho_B$ is too large, the relative motion of the individual fibers will be severely restricted, and the spreading of the microbe-inhibiting agent, which is facilitated by such motion, especially during vigorous use of the article, will be curtailed.

In determining the appropriate design parameters, the following design equation relates several of the key parameters:

$$\rho_B C_B = C_{MI} x_o \quad (3)$$

It is generally necessary that $C_B$ be much greater than the minimum inhibitory concentration. This is because, unless the agent is extremely mobile (which is not desirable due to durability concerns), the agent does not homogenize. For a considerable period of time, it retains notably higher concentrations near the source (initially microbe-inhibiting) fibers. Thus, although $C_B$ is the average concentration in the fiber assembly, much of the assembly will be at a significantly lower concentration.

From tests using 2,4,4'-trichloro-2'-hydroxydiphenol, which is representative of diffusing microbe-inhibiting agents, the following design parameters were determined.

1. $C_B$ should be greater than 0.001%; preferably greater than 0.01%; and most preferably greater than 0.05%.
2. $\rho_B$ should be between 0.1% and 15%; preferably between 0.6% and 10%; and most preferably between 1% and 8%.
3. Once $C_B$ and $\rho_B$ are selected, the left-hand side of Equation (1) is determined; and $C_{MI}$ and $x_o$ are picked so that they are consistent. FIG. 4 shows $x_o$ as a function of $C_{MI}$ for several values of the $\rho_B C_B$-product (in units of $\%_2$). For a particular desired $\rho_B C_B$-product, one can determine the appropriate $x_o$ to use for a given $C_{MI}$ (or vice-versa).

It should be noted that $C_{MI}$ cannot be arbitrarily large; it must be below a value at which the incorporation of the agent causes significantly detrimental effects to the mechanical or chemical stability or integrity of the fiber.

For a given $C_B$, it is preferred that $f_{MI}$ be as large as possible (its maximum value is one), i.e., $C_{MI}$ be as low as possible. For example, it is preferable to have a fiber blend comprising 50% initially microbe-inhibiting fiber with an agent concentration of 0.25% rather than a blend comprising 25% initially microbe-inhibiting fiber with an agent concentration of 0.5%. The larger $f_{MI}$ is, the less one needs to rely on diffusion of the microbe-inhibiting agents. Preferably $f_{MI}$ is between 0.3 and 4.5%.

Zone-of-Inhibition Method

This method requires estimating the effective extent(s) of the zone-of-inhibition, $R_{ZI}$. It should be noted that the ranges of $R_{ZI}$ are essentially phenomenological parameters. They are best measured under conditions similar to those present during use of the pet article. Means for conducting such measurements are given below.

In FIG. 3, the zone-of-inhibition 36 is represented by the region within the dashed lines surrounding the initially microbe-inhibiting fibers 34. It is seen that the zone 36 encompasses regions of the initially non-microbe-inhibiting fibers 32.

For larger materials, the zone of inhibition is often reported simply as a distance—without any reference to the size of the material. For fine fibers, however, the effective zone of inhibition can diminish with the size of the fiber. The physics of the zone of inhibition is complex, but its diminishment in finer fibers may be seen as due in part to the diminished capacity (defined as the total amount of agent that can leach from the fibers) of finer fibers. Values of the extent of the zone of inhibition typically reported for large samples are generally not appropriate for fine fibers. Further, standard tests for the zone of inhibition examine the extent of the inhibition into a relatively solid material (e.g., agar gel). In a stuffed pet article, one is interested in the zone of inhibition as it diffuses into the surrounding fibrous medium.

When a fiber provided with a diffusing microbe-inhibiting agent is combined with conventional fiber, it is generally desired that nearly all the fibers be within the zones of inhibition of the initially microbe-inhibiting fibers. One can obtain an estimate of the fraction of the entire blend, $\zeta$, which is within a zone of inhibition by making an analogy to the Formal Theory of Phase Transformations (e.g., see J. W. Christian, *The Theory of Transformation in Metals and Alloys*, Pergamon Press, 1975). This theory describes the volume fraction of a material that has undergone a phase transformation.

If only a few initially microbe-inhibiting fibers are within an initially non-microbe-inhibiting fiber assembly, the total volume within a zone of inhibition is given simply by adding up the volumes of the zones-of-inhibition of the few fibers. When there are sufficiently many initially microbe-inhibiting fibers that the zones-of-inhibition start to overlap—a situation desirable in the present invention—it is necessary to "discount the excluded volume." As a rule-of-thumb, for fibers (i.e., long and thin structures), the fraction of the entire blend, $\zeta$, that is within a zone of inhibition can be estimated as $$\zeta \approx 1 - \exp(-(1+\alpha)^2 x_o) \text{ where} \tag{4}$$

$$\alpha = \frac{R_{ZI}}{r_f} \tag{5}$$

If $\zeta$ is close to unity, nearly all the conventional fiber is within the zones of inhibition of the initially microbe-inhibiting fiber.

For easy application to use with a wide variety of fibers, the effective extent of the zone of inhibition is represented by the dimensionless parameter, $\alpha$, which is equal to the ratio of the radial extent of the zone of inhibition, $R_{ZI}$, to the effective radius of the fibers, $r_f$.

The effective radial extent of the zone of inhibition, $R_{ZI}$, can be estimated by a variety of means. A preferred means begins with the preparation of a blend comprising the initially non-microbe-inhibiting fiber and a small amount (e.g., less than 1% by volume of the entire blend) of microbe-inhibiting fiber. The blend is then placed on a flat surface and spread somewhat, trying to maintain as much as possible the packing density of the fibers at a level comparable to that which is used in the end application. The entire sample is then inoculated with a desired test organism, and the sample is stored for a period of time necessary for the organism to grow appreciably in areas which are not close to microbe-inhibiting fiber (a control experiment, comprising only non-microbe-inhibiting fiber and the inoculating organisms, is performed simultaneously). The sample is then viewed using a microscope, and the effective range of inhibition is noted. Preferably, several measurements should be performed to ensure that one is measuring the range of inhibition accurately. If the degree of microbial growth is insufficient at reasonably long experimental time scales, one can perform the experiments with the fiber blend situated in contact with a known nutrient material (e.g., agar), preferably immersed in the nutrient material (e.g., place the fibers on an agar surface, inoculate, and then deposit more agar on top). Alternatively, for the non-microbe-inhibiting fiber in the blend, one can use a fiber which is known to be particularly susceptible to proliferation of the microbe(s) of interest.

$R_{ZI}$-values obtained by means described above will tend to be conservative, i.e., the "true" values may be somewhat larger. This is because use of the article generally involves mechanical stresses which tend to spread the MI efficacy throughout the amusement article. A static measurement, such as that described above, neglects this.

Directly measuring $R_{ZI}$ can be time-consuming; and the accuracy can sometimes be questionable. It is therefore sometimes preferable to treat $R_{ZI}$ as a phenomenological parameter, i.e., to determine the microbe-inhibiting efficacy on actual articles, and then to back-infer $R_{ZI}$. The determined $R_{ZI}$ can then be used for optimization of the actual design.

Equation (2) is more accurate when $x_o$ is not too large (i.e., less than about 0.6). It also applies more straightforwardly in cases where the fibers are packed more densely. Furthermore, it is generally preferred that, and the equation applies best when, the initially microbe-inhibiting fiber is distributed homogeneously throughout the fiber blend. This can be brought about be mixing the blend well and optionally by providing the fibers with anti-stick and/or anti-static properties.

Figure 5:
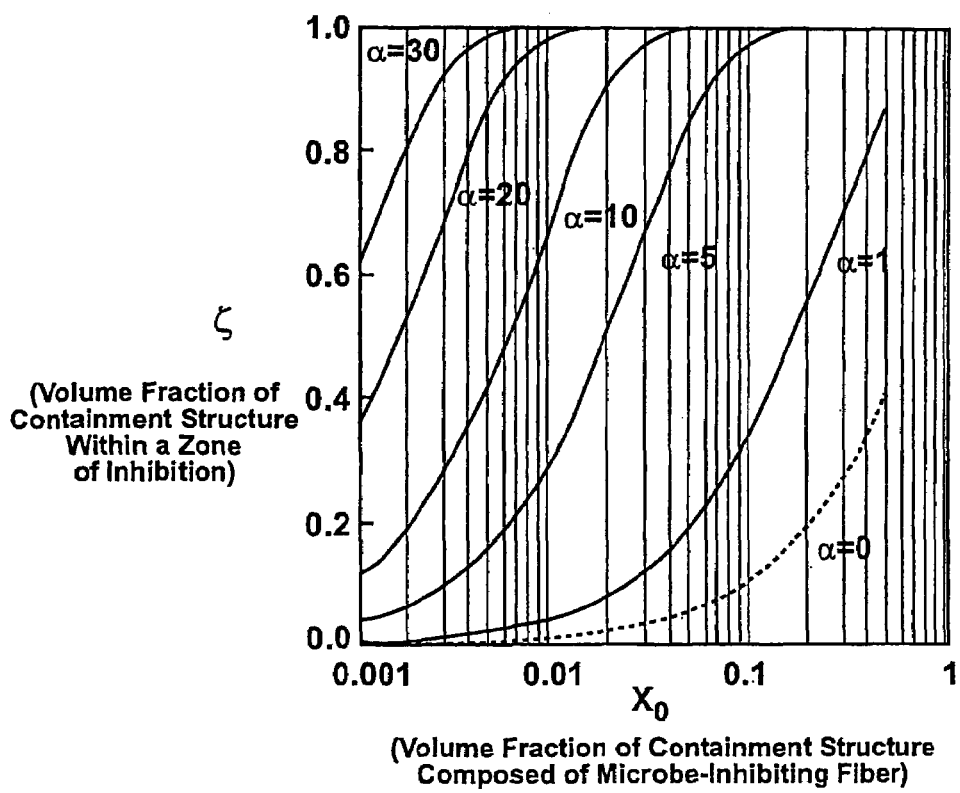
FIG. 5 is a graphical representation of $\zeta$ shown as a function of $X_o$ in accordance with the design parameters of the present invention.

FIG. 5 is a plot of $\zeta$ (the estimated volume fraction of the interior of the containment structure which is within a zone of inhibition) vs. $x_o$ (in dimensionless units) for different values of $\alpha$ (also in dimensionless units) $x_o$ is the volume fraction of the interior of the containment structure which is comprised of initially microbe-inhibiting fiber; and $\alpha$ is the ratio of the effective radial extent of the zone of inhibition to the effective fiber radius. Note that a log-scale is used for the $x_o$-axis.

Amusement articles for pets may also be made from containment structures which are filled with particulate filling materials, with foam materials, or with combinations of these with fibrous materials. For example, one can use a particulate material which is provided with diffusing microbe-inhibiting properties and combine it with conventional non-microbe-inhibiting fiber; or one can mix a foam material in which has been incorporated a microbe-inhibiting agent with a fibrous material.

If the microbe-inhibiting filling material (or some fraction thereof) is more particulate (i.e., three-dimensional) than fibrous, the rule-of-thumb for calculating the fraction of the containment volume that is within a zone of inhibition of the particulate microbe-inhibiting filling material is $$\zeta \approx 1 - \exp(-(1+\alpha)^3 x_o) \text{ where} \quad (4)$$

$$\alpha = \frac{R_{ZI}}{r_f} \text{ and} \quad (5)$$

$$x_o = \frac{VMI_o}{V_c} \quad (6)$$

Here $R_{ZI}$ is the effective radial extent of the zone of inhibition for the microbe-inhibiting fibers used; $r_s$ is the effective radius of the microbe-inhibiting particles used; $VMI_o$ is the volume of microbe-inhibiting particles used in the blend; and $V_c$ is the volume of the interior of the filler containment structure (e.g., sewn fabric for a stuffed pet toy).

If the particles are roughly spherical, $r_s$ corresponds to their average radius. If the particles are appreciably nonspherical, $r_s$ should be interpreted as the effective average radius of the particles (i.e., the relevant behavior is much as if the particles were spherical with radius, $r_s$). Estimates of $r_s$ can be obtained by various means, including direct observation using a microscope. $R_{ZI}$ and $VMI_o$ can be obtained in manners similar to those used for fibers, discussed supra. Considerations similar to those for fibers, as discussed supra, apply with regard to the relationship between the fineness of the particles and the effective radial extent of their zones of inhibition. $V_c$ is obtained in the same manner as in the case where microbe-inhibiting fibers are used, discussed supra.

In practice, the radius of the effective zone of inhibition will diminish with time as the diffusing microbe-inhibiting agent is depleted. The depletion rate is characteristic of the material and the microbe-inhibiting agent used and it will increase with the packing density and the frequency and extent of washing and or abrasion.

It is preferred to construct microbe-inhibiting stuffed pet articles such that ζ is between about 0.5 and 1. It is more preferable to construct such articles such that ζ is between about 0.8 and 1. It is most preferable to construct such articles such that ζ is between about 0.9 and 1. It should be kept in mind that use of the article can spread the microbe-inhibiting efficacy; therefore, the effective ζ of an article may increase with use from its as-manufactured value.

Combinations can be used to create preferred articles for pets. A preferred case is to blend conventional fiber with fiber containing a diffusing microbe-inhibiting agent and use the blend to fill a containment structure whose outer surface has been treated with a strongly bonded microbe-inhibiting agent. Alternatively, one can also use the blend to fill a containment structure whose inner surface has been coated with a latex compound in which a microbe-inhibiting agent is incorporated. The agent in this coating will diffuse to some degree.

Compaction Pre-Treatment of Fiber

As discussed earlier, when diffusing microbe-inhibiting agents are used, the diffusion of the agents from fibers that initially contained the microbe-inhibiting agents to fibers that did not is an important aspect of the resulting microbe-inhibiting efficacy of the article. The kinetics of this diffusion, in terms of distance that the microbe-inhibiting agents diffuse, are governed by an effective diffusion coefficient, D. To expose more fiber to the microbe-inhibiting agent in a given amount of time, one can maintain the fiber in a compacted state.

Markedly increased efficacy can thereby be obtained by maintaining the fiber in a compacted state for a period of time before using it as filling for microbe-inhibiting articles of the present invention. Homogenization of the microbe-inhibiting agent occurs at a greatly accelerated rate when the fibers are so compacted; and toys fabricated from such fiber will possess a relative uniformity of microbe-inhibiting agent concentration that is needed for efficacy in the demanding environment in which the toys are used.

The degrees of compaction should be such that the fiber is at a relative volume fraction of greater than 10%, preferably greater than 14%, and most preferably greater than 18%. Compaction should not be so strong that the fiber is damaged (e.g., compaction levels greater than about 40% may do more harm than good).

The desired compaction time is determined by the diffusivity of the microbe-inhibiting agent from the initially microbe-inhibiting fiber to the initially non-microbe-inhibiting fiber. One can perform diffusion calculations appropriate for a porous medium to determine the appropriate times.

The "relative volume fraction" of the fiber is defined as the fraction of a given volume that is occupied by the fiber material. One way to calculate this is as follows: Take the geometric volume occupied by the fiber (i.e., the volume the fiber appears to occupy); weigh the fiber in this volume; from the known fiber effective density, calculate the volume actually occupied by the fiber; divide this volume by the geometric volume to obtain the volume fraction occupied by the fiber. (If the fiber is of the "hollow" type, allowances must be made.) Increasing the temperature will also increase the effective diffusion coefficient; and if this process can be done cost effectively (which is often a problem) and at a temperature that is below any degradation temperature associated with the microbe-inhibiting agents, it can be a useful aid for homogenization.

Empirical Uses of the Present Teaching

Figure 4:
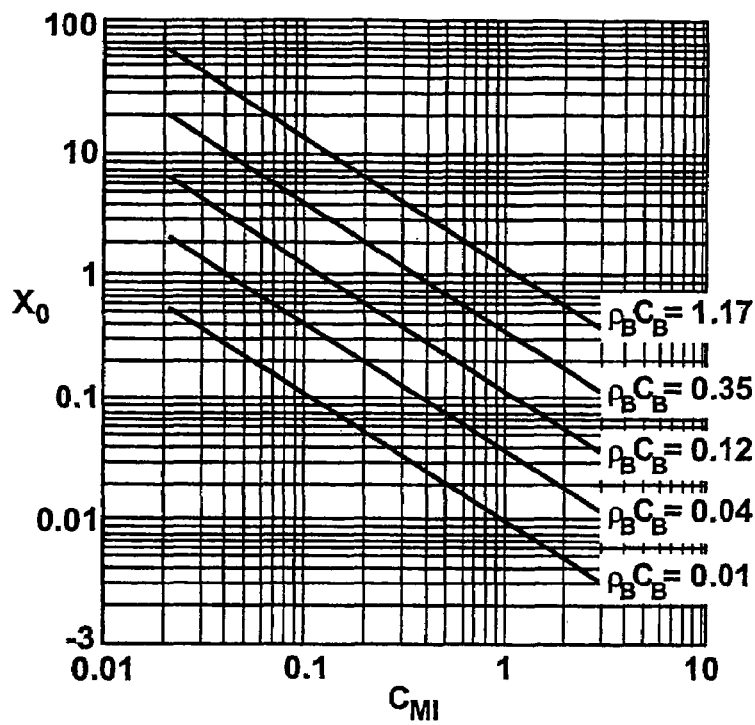
FIG. 4 is a graphical representation of $X_o$ shown as a function of $C_{MI}$ in accordance with the design parameters of the present invention.

Consider a stuffed pet toy with a containment volume of $V_c=908$ cm$^3$ that is to be made using a combination of a diffusing agent microbe-inhibiting triacetate fiber and a conventional non-microbe-inhibiting polyester fiber. The triacetate fiber has a density, ρ, of about 1.32 gm/cm$^3$; and the polyester fiber has a density, ρ, of about 1.39 gm/cm$^3$. For a total blend density $\rho_B=4\%$, and an average blend concentration of $C_B=0.09\%$, the $\rho_B C_B$-product is 0.36 (in units of %$^2$), which is close to the value corresponding to the $\rho_B C_B=0.35$ curve of FIG. 4. Suppose it is desired to use microbe-inhibiting fiber containing 0.3% of an agent similar to 2,4,4'-trichloro-2'-hydroxydiphenol. Using FIG. 4, this corresponds to an $x_o$-value of about 1.2%. This corresponds to a volume of 10.9 cm$^3$, or 14.4 gm of the triacetate fiber. The remaining 2.8% (or 25.4 cm$^3$) of the fill volume is to be occupied by polyester fiber. This corresponds to about 35 gm of the polyester fiber. Thus, the appropriate blend contains 35 gm of polyester fiber and 14.4 gm of triacetate fiber inserted into the 908 cm$^3$ cover material.

Zone-of-Inhibition Uses of the Present Teaching

Consider a stuffed pet toy with a containment volume of $V_c=350$ cm$^3$ that is to be made using a combination of a diffusing agent microbe-inhibiting acrylic fiber having an approximately circular cross-section and a conventional non-microbe-inhibiting polyester fiber. The acrylic fiber has a density, ρ, of about 1.18 gm/cm$^3$ and a denier of 3. The effective radial extent of the zone of inhibition of the fiber is measured to be about 70 μm. The polyester fiber has a density, ρ, of about 1.39 gm/cm$^3$.

A 3 denier fiber with density 1.18 gm/cm$^3$ possesses an effective average radius of about 6.7 μm. α for this system is therefore about 10.4. The behavior of this fiber will be close to that described by the "α=10" curve in FIG. 5. From the curve, it is seen that ζ approaches unity at $x_o$-values of about 4%–6%. This corresponds to a volume of about 14–21 cm$^3$ or a mass of about 17–25 gm. Therefore, to ensure that most of the interior of the containment structure is within a zone of inhibition, it is necessary to include about 17–25 gm per toy of the microbe-inhibiting acrylic fiber. Assuming it is desired to for the containment structure to have a total filled volume of 10%, one must include a volume fraction of the polyester blend of about 6%–4%. The corresponds to a volume of about 21–14 cm$^3$ or a mass of about 29–19 gm. The fibers should be well blended together.

Generally, the denier of the fibers should preferably be between 0.8 and 20, and most preferably between 1 and 15. The cut length of the fiber should preferably be between 0.1 inches and 8 inches, most preferably between 0.4 inches and 5 inches.

Manufacture of Microbe-Inhibiting Fillers and Containment Structures

The manufacture of a textile-based stuffed pet toy typically begins with the conversion of the textiles from roll form to the appropriate shapes and sizes via die-cutting. The shapes are usually complex, with irregular perimeters. These materials comprise the containment or cover material of the stuffed toy. For the case of a simple toy, the cover will be formed from two halves cut from the textile.

The cut containment materials are then sewn around their perimeter, but not closed; an aperture is left for subsequent stuffing of the toy. The size of the aperture is chosen to be compatible with the filling apparatus and to allow for adequate containment of the stuffing for the period of time before the aperture is closed. For toys of typical sizes and for typical filling apparatuses, the aperture possesses a dimension of about 0.5–2 inches. During the sewing process, the containment materials can optionally be in an "inside-out" configuration so that the seam is concealed in the final product.

Microbe-inhibiting properties can be conferred to the toy by using a filling that is in whole or in part comprised of microbe-inhibiting material by using a containment material which in whole or in part possesses microbe-inhibiting properties, or by some combination of the two. The materials can be made microbe-inhibiting by suitably treating them, e.g., spraying with or soaking in a microbe-inhibiting solution, or by incorporating microbe-inhibiting agents during their manufacture.

The filling material is weighed, shredded, and blended (either manually or through a shredded/picker) and either hand-stuffed into the toy or blown into the toy using a blowing machine. After filling, the aperture is closed, e.g., by hand-sewing, machine-sewing, gluing, stapling, etc.

Another type of filling that can be used is comprised of a blend of conventional polyester non-microbe-inhibiting fiber and microbe-inhibiting particulate matter in which the microbe-inhibiting properties of the particulate are provided by incorporation of a diffusing microbe-inhibiting agent. The microbe-inhibiting particulate matter can be obtained in a variety of ways. For example, one can form polystyrene beads incorporated with Microba microbe-inhibiting agent or property. One can also incorporate microbe-inhibiting agents into various zeolitic particulates. The zone of inhibition corresponding to the particulate is essentially three-dimensional in character. Relative to the fibrous (essentially two-dimensional) case, and to the extent that $\alpha$ remains constant, a lesser volume fraction of the particles ($x_o$) is generally required for most of the containment material to be within a zone of inhibition. In this case, the relative composition should be such that the antimicrobial particulate comprises a volume fraction of the containment structure of more than about 1%, preferably more than about 3%, and most preferably more than about 5%. The remaining (non-microbe-inhibiting) fiber is added in an amount such that the fiber comprises between 0.1% and 15%; preferably between 0.6% and 10%; and most preferably between 1% and 8% of the volume fraction of the total containment structure.

In the above case, however, the provision that $\alpha$ remains constant can be quite restrictive. This will generally require particulates with diameters in the range of tens of microns. It will frequently be undesirable for such small particles to be free within the amusement article (they can escape from the containment structure and be breathed or otherwise taken up by the body of the pet or its owner). In practice, therefore, when beads or particles are used as part of a fill, they are made to be larger (typically on a scale of millimeters). This size increase causes $\alpha$ to become smaller, which reduces efficacy for a given volume fraction of material (see FIG. 1), but it provides for a safer and more attractive article; and one can simply increase $x_o$ to compensate.

Fillings in which the fiber has microbe-inhibiting properties and the particulate does not can also be used. In this case, however, because the particulate is being used primarily for its filling properties (as opposed to microbe-inhibiting properties), there is no downside to making the particles larger. The effective diameter of the particulate should be greater than about 0.50 mm, preferably greater than about 0.75 mm, and most preferably greater than about 1.00 mm.

Shredded foam, polystyrene beads, polyester, and/or recycled or virgin fiber can be substituted, in part or in whole, for conventional fiber and blended with antimicrobially-treated fiber as per the above. One can alternatively or in addition inject a microbe-inhibiting foam precursor into the aperture and form the foam in-place.

Cut foam, all or in part microbe-inhibiting, can be used for filling in a variety of ways. For example, it can be cut to roughly the same size and shape as the cut halves and included in the interior of the article before sewing; or short strips of foam can be obtained and used as a fill in manners similar to that of fiber.

Microbe-inhibiting properties can be imparted to the containment material by spreading the rolls of the containment material and spraying their surface(s) with a suitable microbe-inhibiting solution, e.g., a solution of an agent comprising a microbe-cidal quaternary ammonium compound functionality and a silane coupling agent functionality. A preferred microbe-inhibiting agent of this type is Dow Corning 5700 (active ingredient: 3-trimethioxysilylpropyl dimethyloctadecyl ammonium chloride). If one is treating a porous material with a moderate-to-good moisture regain, and if purified water is the predominant solvent, the concentration—as a percentage of the weight of the material being treated) should be approximately 0.01–1%. The preferred predominant solvent is purified water; but other solvents, such as methanol and isopropanol can be used in conjunction with the purified water. If desired, treatment can be carried out using a treatment bath rather than by spraying. In either case, siloxane condensation catalysts can be used to enhance condensation reactions and to induce a stronger bond of the agents to the surface of the material.

Attractive microbe-inhibiting amusement articles for pets can also be made without using any fiber-filling. If a very high-pile cover material (made to be microbe-inhibiting by means discussed above) is used, the toy may have an adequate feel for use, and the cost is reduced considerably relative to a toy containing fiber. One must ensure, however, that the entire cover is directly incorporated with microbe-inhibiting properties, or that a sufficient fraction of the fibers comprising the cover material were treated with a diffusing agent and that the agents has been effectively transferred to the other fibers.

Manufacture of Microbe-Inhibiting Linings

Another means of imparting microbe-inhibiting properties to the toy is to utilize a microbe-inhibiting liner. This means can be used alone or in conjunction with the use of microbe-inhibiting filler and/or containment materials. For example, microbe-inhibiting flexible plastic sheets can be die-cut along with the containment material. These plastic sheets can then be placed on the backside (i.e., inner side) of the die-cut containment materials before sewing. The subsequent sewing process will thereby incorporate a microbe-inhibiting plastic layer on the inside of the containment material. The toys can then be filled in the usual manner. Because the resulting containment structure can be relatively impermeable to air, if an air-driven filling machine is used for filling, it is useful to provide an extra aperture to allow for the air to escape. To avoid having to close another aperture in the final stage of manufacture, however, it is generally preferable to use only one aperture and perform the filling in such a way that air can escape from the aperture through which filling is carried out.

Plastic linings are effective both because they can be treated with microbe-cidal agents and because they can be obtained relatively impermeable to microbes, liquids, dirt, dust, excrement, etc. Even if the linings do not possess microbe-cidal properties, they can still possess significant microbe-inhibiting properties by virtue of their impermeability to microbes and to material which encourages the proliferation of microbes.

Microbe-inhibiting vinyl sheet is a preferred Material for the lining. The material can comprise a microbe-cidal treated vinyl sheet or it can comprise a laminate structure with at least one layer comprising a microbe-cidal treated plastic sheet. A difficulty with this type of material is that it tends to be somewhat stiff and the sewing process tends to require more dexterity and control, resulting in less efficient manufacturing. To ameliorate this difficulty, softer, more pliable plastics are preferred. These can be obtained, e.g., by using thin vinyl sheeting or increased concentrations of non-microbially-digestible plasticizer in manufacturing the plastic. Alternatively, one can bond the plastic sheet to the fabric. The bond can be weak (as via static electricity or a weak adhesive) or it can be strong (e.g., utilizing a coupling agent or an effective plastic-fabric adhesive).

A lining can be employed in the form of a bag inside the toy. For example, a containment structure for the toy can be constructed in the usual manner. A bag is then constructed by die-cutting two plastic cut halves in approximately the same size and shape as the containment material. The appropriately shaped bag with an aperture can then be formed from the two plastic cut halves by placing one cut half on top of the other and applying heat to the perimeter. The bag is inserted into the containment structure, the bag is filled with the filling material while it is within the containment, and the aperture is sealed.

When a lining is used, filling can be facilitated by including in the shape of the lining a notch that protrudes from the aperture. The notches can help prevent fill from entering the space between the lining and the outer containment material.

A preferred means for incorporating a lining without increasing the dexterity and control required to attach the lining to the containment material is to employ a microbe-inhibiting soft fabric rather than a microbe-inhibiting plastic sheet. Microbe-inhibiting cotton is a preferred material, as are polyester/cotton blends and acrylic-based fabrics. These fabrics are generally permeable to microbes, liquids, dirt, dust, excrement, etc., and hence do not possess the microbe-impenetrable characteristics of the plastic sheeting used.

Rather than using a separate lining material, one can apply a coating of microbe-inhibiting plastic to the backside of the fabric comprising the containment material. It is preferred to use a latex suspension to which a microbe-inhibiting agent has been added. The resulting suspension can be applied to the backside of the containment material using, e.g., a brush or a roller. The resulting latex coating provides microbe-cidal protection due to the incorporated microbe-cidal agent; microbe-impenetrable protection (if the coating is continuous across the fabric); and desirable physical characteristics such as increased dimensional stability, increased durability, and increased resilience. It can also facilitate cutting operations. Such latex coatings are particularly efficacious because they can be applied so that the resulting fabrics do not have an excessively stiff feel. Polyurethane coatings with added microbe-inhibiting agents are also preferred.

Non-Woven Articles

A unique type of amusement article for a pet is composed primarily from an extremely high-loft non-woven material structure, such as those used in filtration systems. The high-loft, low density material can be prepared by known techniques (e.g., from extruded continuous filaments or from fiber webs or batts strengthened by bonding between or among fibers). The fiber bonding can be brought about by heating (including the use of low-melting coatings or sheath), by using adhesives, stitch-bonding, or mechanical interlocking (e.g., needling). The material can then be die-cut into desired shapes (e.g., fish, mouse, star, cloud, disc, bone, bear, etc).

If the fibers comprising the non-woven structure are very well-bonded to each other, the die-cut toy can be used as is. If they are not sufficiently well-bonded, one can seal the outer perimeter of the toys by some other means (e.g., local heating, stitching, serging, tacking, etc.).

These toys can be made microbe-inhibiting by use of microbe-inhibiting fibers or fiber blends, where the fibers are incorporated with a microbe-inhibiting agent at the time of their manufacture or post-treated with a microbe-inhibiting agent. If an agent of the diffusing type is used, only a fraction of the fibers is required to be initially microbe-inhibiting (the magnitude of this fraction is determined in the same manner as for the fiber-fill). If the agent is of the strongly bonded type, it is preferred that most (if not all) of the fiber be initially microbe-inhibiting. Preferred base materials are polyester or olefin fibers or filaments.

It is important to ensure that procedures used commonly in non-woven manufacture (e.g., heat-bonding, application of adhesives, etc.) does not diminish the microbe-inhibiting efficacy of the finished product. For example, heat-bonding must be done at a temperature lower than the degradation temperature of the microbe-inhibiting agents used. Adhesives or low-melt outer coatings must not block the diffusion of microbe-inhibiting agents (in the diffusing agent case) or overcoat the microbe-inhibiting surface (in the strongly-bonded agent case).

In cases where the adhesive or other coatings only need to be applied to a fraction of the fibers or filaments and the microbe-inhibiting agents only need to be incorporated into a fraction of the fibers or filaments, it is preferred that these fractions be separate. It cases where this is not advisable (e.g., the fiber fraction which needs to be incorporated with a microbe-inhibiting agent is too large, or a strongly bonded agent is being used), it is preferred to post-treat the high-loft batting when it is in roll form (i.e., after it is already bonded), using a bath or spray technique.

A particularly preferred non-woven material for the present invention is a very high-loft low density type such as those used in filtration systems. The materials can be purchased from a filter manufacturer in roll form and then post-treated or can be incorporated in the fibers that comprise the filter.

The desired thickness of the non-woven material for these articles will vary with the lateral size of the article, the type of perimeter bonding used, and with consumer preference. When perimeter bonding is brought about by sewing the perimeter, and the lateral size of the article is relatively small (e.g., shortest dimension on the order of several times the thickness), the sewing tends to decrease dramatically the average thickness of the articles, and the starting material should therefore be several times thicker than the desired final thickness. Generally, desired average thickness of the finished toys is on the order of inches (about 0.5–4 inches).

In one embodiment, the non-woven material can be enclosed in an open-mesh bag or netting material made of a synthetic resin or natural material to maintain the integrity of the non-woven material while permitting the pet to engage or feel the non-woven material. The article may be especially attractive to cats.

Odor-Control

Pet toys often have a tendency to emit odors. There are numerous causes for such odors, many of which are related to microbes. It is therefore an additional benefit to the use of pet articles possessing microbe-inhibiting properties that such articles will frequently display a reduced tendency to develop odors.

A wide variety of anti-odor (or deodorizing) compositions are known in the art. Odor masking, the intentional concealment of one odor by another odor, is perhaps the most common means for controlling odors. Odor masking on fabrics can be accomplished using various perfumes, colognes, etc. Relatively high levels of the masking agent are often required for adequate concealment of the odor.

Odor modification, where the odor is changed, as by chemical modification, can also been used; and it is frequently preferred over odor masking. The odor can be modified to become less offensive or can be diminished or neutralized.

In many cases it is preferred to use an odor-absorbing material rather than a masking or modification agent. Odor absorbing materials are often "broad spectrum" in nature, i.e., they are effective in neutralizing many different odor-causing agents. Common odor absorbing materials include activated charcoal and zeolites. These materials are typically used in a particulate form. They can be incorporated into the pet article in a variety of ways, such as directly into the materials comprising the article during their manufacture; or added to some component of the article during its manufacture; or adhered to some component(s) of the article.

A further advantage of microbe-inhibiting pet toys of the present invention is that, if it is desired to incorporate deodorizing, odor-modifying, or odor-masking materials, less such materials are needed than in a comparable article which did not possess microbe-inhibiting properties.

A preferred class of zeolites for use as odor absorbents are the intermediate silicate/aluminate zeolites. The intermediate zeolites can be characterized as having silica/alumina molar ratios of less than about 10. With regard to the present invention, intermediate zeolites are often preferred over "high" zeolites. The intermediate zeolites possess a higher affinity for amine-type odors; they are generally more efficient in odor absorption because they typically have larger surface areas; they are generally more moisture tolerant; and they retain more of their odor absorbing capacity in water than do "high" zeolites.

Carbonaceous materials that serve effectively as absorbents for organic molecules are often referred to as activated carbon or activated charcoal. Many of these materials are suitable for use in the present invention. They are available from commercial sources under such trade names as Calgon-Type CPG, Type PCB, Type SGL, Type Cal, and Type OL.

In support of the present invention the following experiments were conducted:

EXAMPLE NO. 1

A 1000 $cm^3$ cover structure in the shape of a disc is to be filled with a fiber blend; and the total blend is to comprise 3.75% of the total containment volume. The average blend concentration of the microbe-inhibiting agent is to be greater than 0.14%. A triacetate fiber (density=1.32 $gm/cm^3$) in which was incorporated 0.5% triclosan antimicrobial agent during its manufacture, as well as conventional polyester fiber (density=1.39 $gm/cm^3$) are to be used.

The filling is prepared using the design equations (1)–(6) set forth above. It is necessary to have the microbe-inhibiting triacetate fiber occupy a volume fraction of the containment structure equal to about 1.1%, and to have the conventional polyester fiber occupy a volume fraction of the containment structure equal to about 2.6%. 14.8 gm of the microbe-inhibiting triacetate fiber possessing a denier of about 6 and cut to a length of about 2") was therefore blended with 36.5 gm of conventional polyester fiber (possessing a denier of about 6 and cut to a length of about 2"). In this case, the average blend concentration, $C_B$, is about 0.15%.

EXAMPLE NO. 2

A 500 $cm^3$ cover structure in the shape of a bone is to be filled with a fiber blend; and the total blend is to comprise 2.8% of the total containment volume. The average blend concentration of the microbe-inhibiting agent is to be greater than 0.38%. An acrylic fiber (density=1.18 $gm/cm^3$) in which was incorporated 0.65% triclosan antimicrobial agent during its manufacture, as well as conventional nylon fiber (density=1.14 $gm/cm^3$) are to be used.

The filling is prepared using the design equations (1)–(6) set forth above. It is necessary to have the microbe-inhibiting acrylic fiber occupy a volume fraction of the containment structure equal to about 1.7%, and to have the conventional nylon fiber occupy a volume fraction of the containment structure equal to about 1.1%. 9.9 gm of the microbe-inhibiting acrylic triacetate fiber (possessing a denier of about 3.5 and cut to a length of about 1.5") was therefore blended with 6.4 gm of conventional nylon fiber (possessing a denier of about 5.5) and cut to a length of about 1.5"). In this case, the average blend concentration, $C_B$, is about 0.39%.

EXAMPLE NO. 3

A 2000 $cm^3$ cover structure in the shape of a bear is to be filled with a fiber blend; and the total blend is to comprise 4% of the total containment volume. The average blend concentration of the microbe-inhibiting agent is to be about 0.11%. A polypropylene fiber (density=0.93 $gm/cm^3$) in which was incorporated 0.2% Tri-n-butyltin maleate (Ultra Fresh DM-50) antimicrobial agent during its manufacture, as well as regular polyester fiber (density=1.39 $gm/cm^3$) are used.

Using the design equations (1)–(6) set forth above, it is necessary to have the microbe-inhibiting polypropylene fiber occupy a volume fraction of the containment structure equal to about 2.2%, and to have the conventional polyester fiber occupy a volume fraction of the containment structure equal to about 1.8%. 40.9 gm of the microbe-inhibiting fiber (possessing a denier of about 4 and cut to a length of about 2") was therefore blended with 50.0 gm of conventional polyester (with a denier of 5 and cut to a length of about 2").

EXAMPLE NO. 4

The cover or containment material was constructed from synthetic lambswool, also known as "fleece," or shearling. The maternal has two sides: a fleece side, which simulates the fleece of a lamb; and a backing or back-side. The synthetic lambswool may be obtained from Tex-Tenn Corp., (Gray, Tenn.). It is comprised primarily of polyester, but is blended with a small amount of acrylic. The material has a weight of 17.5 oz/linear yard and is obtained on 60"-wide rolls.

Four rolls are suspended on a rack, and the synthetic lambswool is pulled from the rolls in tandem and fed onto the bed of the die-cutting press. A steel-rule die in the shape of a bone (long dimension about 7") is placed on top of the layers of synthetic lambswool and beneath, the head of the die press. The head of the die press is then brought down onto the steel-rule die, whereupon it cuts through the four layers of fabric in a single strike to yield four pieces of bone-shaped synthetic lambswool. The pieces are referred to as "cut halves."

Two cut halves are then placed together such that the fleece sides are facing each other. The two cut halves are then sewn together along their mutual perimeter, leaving a 1–2"-wide orifice for later insertion of the filling. The sewn material is then flipped inside-out such that the fleece side was on the exterior. The volume of the bone-shaped containment structure is obtained by filling a nominally identical unfilled containment structure with small, plastic beads and subsequently transferring the beads to a large graduated cylinder. The volume is readily obtained from the markings on the graduated cylinder. The volume of the containment thereby obtained is about 900 cm$^3$. The mass of the cover structure is about 20.7 gm.

It is desired to fill the toy to a volume fraction of about 3.5%.

The microbe-inhibiting fiber used is acrylic. The fibers are solution-spun, and triclosan is added to the spin dope to produce fibers containing about 0.2% triclosan. The fiber is cut to a length of 1", and is blended with conventional acrylic fiber, which is also solution-spun and cut to a length of about 1". Both fibers possess a denier of about 3.5. The average blend concentration, $C_B$, equal to about 0.08%.

From the design equations (1)–(6) set forth above, it is determined that it was necessary to have the microbe-inhibiting acrylic fiber occupy a volume fraction of the containment structure equal to about 1.4%, and to have the conventional acrylic fiber occupy a volume fraction of the containment structure equal to about 2.1%. 14.9 gm of the microbe-inhibiting acrylic fiber is therefore blended with 22.3 gm of conventional acrylic fiber. The fill is then inserted through the aperture of the cover structure, and the aperture is then sewn closed. A stuffed dog toy in the shape of a bone, where the filling is provided with microbe-inhibiting properties, is thus obtained.

EXAMPLE NO. 5

Bone-shaped fleece-type toys are constructed in the same manner and with the same dimensions as in Example No. 4, except that the filling is incorporated into the toy using a blowing/filling machine. It is desired to fill about 200 toys. The calculations in Example No. 4 are scaled-up by a factor of 200. About 3.0 kg of the microbe-inhibiting acrylic fiber are therefore blended with about 4.5 kg of conventional acrylic fiber. The material is placed in the hopper of the blowing/filling machine. About 37.2 gm of the fiber blend is blown into the cover structure. (There is a measuring scale near the operator of the blowing/filling machine; the toy periodically placed on the scale; and since the cover weighs 20.7 gm, each toy is filled until its mass is about 57.9 gm. Operators soon become sufficiently skilled than frequent measuring is not necessary).

The aperture is then sewn closed. Stuffed dog toys in the shape of bones, where the filling is provided with microbe-inhibiting properties, are thus obtained.

EXAMPLE NO. 6

The material comprising the containment structure of the toy is provided with microbe-inhibiting properties by virtue of a topical treatment. The treatment is carried out before the shapes are cut with the die press. A roll of the synthetic lambswool is unrolled and taken up onto an initially empty roll. While the fabric is in the unrolled state between the two rolls, it is sprayed with a microbe-cidal solution on the fleece side.

The solution is obtained by mixing 5 oz. of Quat EPA 12 with 1 gallon of purified water. (The active ingredient of Quat EPA 12 is the quaternary ammonium compound, alkyl dimethyl benzyl ammonium chloride.)

After the synthetic lambswool is treated, it is used in the manner described in Example No. 4 to construct a bone-shaped containment structure. It is desired to fill the cover material only with non-microbe-inhibiting fiber, and to fill it to a volume fraction of about 3.5%. The containment structure is filled with about 43.8 gm of conventional polyester fiber. A stuffed dog toy in the shape of a bone and possessing microbe-inhibiting properties is thus obtained.

EXAMPLE NO. 7

The toy is provided with microbe-inhibiting properties by incorporating a liner. Artificial lambswool and white Staph-Chek Microvent Comfort fabric (a textile backed thermoplastic film sold by Herculite Products, Inc.) are die-cut using a bear-shaped die (about 7" on the long dimension). As in Example No. 4, the two cut halves of the artificial lambswool are placed with their fleece sides facing one another (the back-sides facing outward). The cut halves of the Staph-Chek Microvent Comfort fabric are then placed directly in contact with the two backsides. The four-layer composite is then sewn and inverted as in Example No. 4, resulting in a bear-shaped containment structure with a microbe-inhibiting liner.

It is desired to fill the cover material only with non-microbe-inhibiting polyester fiber, and to fill it to a volume fraction of about 3.5%.

The volume of the bear-shaped cover structure is obtained by filling a nominally identical unfilled containment structure with small, plastic beads and subsequently transferring the beads to a large graduated cylinder. The volume is readily obtained from the markings on the graduated cylinder. The volume of the containment thereby obtained is about 1240 cm$^3$. It is desired to fill the toy to a volume fraction of about 3.5%. The containment structure is therefore filled with about 60.3 gm of conventional polyester fiber. A stuffed pet toy in the shape of a bear and possessing microbe-inhibiting properties is thus obtained.

EXAMPLE NO. 8

The toy is provided with microbe-inhibiting properties by incorporating a microbe-cidal liner. They toy is constructed in the same manner and with the same dimensions as in Example No. 7, except that the liner material is die cut from sheets of Aegis High Density (tight-weave antibacterial fabric available from Precision Fabrics Group, Inc.).

EXAMPLE NO. 9

The toy is provided with microbe-inhibiting properties by incorporating a microbe-cidal liner. They toy is constructed in the same manner and with the same dimensions as in Example No. 7, except that the liner material is die cut from sheets of Staph-Chek Synergy fabric (A synthetic textile fabric with a thermoplastic backing and a microbe-cidal agent in the adhesive between the fabric and the backing sold by Herculite Products, Inc.).

EXAMPLE NO. 10

The toy is hereby provided with microbe-inhibiting properties by incorporating a microbe-cidal liner. They toy is constructed in the same manner and with the same dimensions as in Example No. 7, except that the liner material is die cut from sheets of Staph-Chek Microvent Soft fabric (A non-woven textile with a thermoplastic backing and containing microbe-cidal properties sold by Herculite Products, Inc.).

EXAMPLE NO. 11

The toy is hereby provided with microbe-inhibiting properties by incorporating both a microbe-cidal liner and microbe-cidal fill. They toy is constructed in the same manner and with the same dimensions as in Example No. 8, except that in the present example, a microbe-inhibiting fiber blend is used. All of the fiber is acrylic. The fibers are solution-spun, and triclosan is added to the spin dope to produce fibers containing about 0.5% triclosan. The fiber is cut to a length of 1". It is blended with conventional acrylic fiber, which is also solution-spun and cut to a length of about 1". Both fibers possess a denier of about 3.5. It is desired to have a total fill volume fraction of about 3.5%, and an average blend concentration, $C_B$, equal to about 0. 1%.

From the design equations (1)–(6) set forth above, it is determined that it was necessary to have the microbe-inhibiting acrylic fiber occupy a volume fraction of the containment structure equal to about 0.7%, and to have the conventional acrylic fiber occupy a volume fraction of the containment structure equal to about 2.8%. 10.2 gm of the microbe-inhibiting acrylic fiber is therefore blended with 40.0 gm of conventional acrylic fiber.

The fill is then inserted through the aperture of the cover structure, and the aperture is then sewn closed. A stuffed dog toy in the shape of a bear, where the filling is provided with microbe-inhibiting properties, is thus obtained.

EXAMPLE NO. 12

A roll of Polyfill Extra-Loft Antibacterial Batting (a non-woven polyester treated with Dow Corning 5700 antimicrobial agent, available from Fairfield Processing Corporation) is spread out on a cutting table. Seven rolls are suspended on a rack, and the material is pulled from the rolls in tandem and fed onto the bed of the die-cutting press. A steel-rule die in the shape of a mouse (long dimension about 4") is placed on top of the layers of the material and beneath the head of the die press. The head of the die press is then brought down onto the steel-rule die, whereupon it cuts through the seven layers of fabric in a single strike to yield seven pieces of mouse-shaped non-woven material. The mutual outer perimeter of the seven-layer structure is then serged on a serging machine. This serves as an attractive pet toy, particularly for cats without any edge treatment.

EXAMPLE NO. 13

A 1.5" non-woven filter composed of blue polyester fibers (from National Filter Media Corporation) is obtained in roll form. Two rolls are suspended on a rack, and the material is pulled from the rolls in tandem and fed onto the bed of the die-cutting press. A steel-rule die in the shape of a mouse (long dimension about 4") is placed on top of the layers of the material and beneath the head of the die press. The head of the die press is then brought down onto the steel-rule die, whereupon it cuts through the two layers of fabric in a single strike to yield two mouse-shaped toys. These toys serves as attractive pet toys, particularly for cats.

EXAMPLE NO. 14

A high-loft non-woven batting material composed of 15% cellulose acetate fiber and 85% polyester fiber, in which the cellulose acetate fiber has been incorporated with Microban antimicrobial agent at the time of manufacture of the fiber, is obtained in roll form (Carpenter Company). The material has a thickness on the order of 0.5". 8 layers of the material are placed onto the bed of a die-cutting press. A steel-rule die in the shape of a cloud (long dimension about 5") is placed on top of the layers of the material and beneath the head of the die press. The head of the die press is then brought down onto the steel-rule die, whereupon it cuts through the eight layers of fabric in a single strike to yield eight pieces of cloud-shaped non-woven material. After ensuring that the eight pieces are aligned, the outer perimeter is serged on a serging machine. The resulting toy is especially attractive for cats.

EXAMPLE NO. 15

A polypropylene particulate is prepared containing about 0.2% Triclosan. An amount necessary to fill a cover structure to a volume fraction of about 35% is placed into a mesh bag, which is then sewn shut. A pair of cut halves are prepared. Before sewing, however, part of the edge of the mesh bag is aligned with part of the edge of one of the cut halves. The cut halves are then sewn in the usual manner, leaving an aperture large enough for the sewn cover/mesh bag combination to be inverted. After inversion, the aperture is sewn shut.

EXAMPLE NO. 16

A bone-shaped cover structure is made in the same manner and with the same dimensions as in Example No. 4. The cover structure is then filled with a well-mixed blend of 38 gm of acrylic fiber (incorporated with 0.2% triclosan; denier=3.5; cut length=1") and 65 gm of Poly-Pellets (polypropylene beads, available from Fairfield Processing Corporation). The aperture of the filled cover structure is then sewn closed.

EXAMPLE NO. 17

The cover or containment material was constructed from Aegis High Density fabric (a tight-weave antibacterial fabric available from Precision Fabrics Group, Inc.). Four rolls are suspended on a rack, and the fabric is pulled from the rolls in tandem and fed onto the bed of the die-cutting press. The same die as in Example No. 4 is placed on top of the layers of the fabric and beneath the head of the die press. The head of the die press is then brought down onto the steel-rule die, whereupon it cuts through the four layers of fabric in a single strike to yield four pieces of bone-shaped fabric. The pieces are referred to as "cut halves."

Two cut halves are then placed together such that they are superimposed. The two cut halves are then sewn together along their mutual perimeter, leaving a 1.5"-wide orifice for later insertion of a filling. The sewn material is then flipped inside-out such that the sewing cannot be seen.

The toy is to be filled to a volume fraction of about 3.5%.

The microbe-inhibiting fiber used is acrylic. The fibers are solution-spun, and triclosan is added to the spin dope to produce fibers containing about 0.2% triclosan. The fiber is cut to a length of 1", and is blended with conventional acrylic fiber, which is also solution-spun and cut to a length of about 1". Both fibers possess a denier of about 3.5. The average blend concentration, $C_B$, equal to about 0.08%.

From the design equations (1)–(6) set forth above, it is determined that it was necessary to have the microbe-inhibiting acrylic fiber occupy a volume fraction of the containment structure equal to about 1.4%, and to have the conventional acrylic fiber occupy a volume fraction of the containment structure equal to about 2.1%. 14.9 gm of the microbe-inhibiting acrylic fiber is therefore blended with 22.3 gm of conventional acrylic fiber.

The fill is then inserted through the aperture of the cover structure, and the aperture is then sewn closed. A stuffed dog toy in the shape of a bone, where the filling is provided with microbe-inhibiting properties, is thus obtained.

EXAMPLE NO. 18

A bone-shaped toy is made in the same manner, with the same dimensions, and with the same filling as in Example No. 17; but the cover structure is instead made from rolls of Staph-Chek Synergy fabric (Herculite Products, Inc.).

EXAMPLE NO. 19

The cover or containment material was constructed from light nylon fabric. Eight rolls are suspended on a rack, and the fabric is pulled from the rolls in tandem and fed onto the bed of the die-cutting press. A steel-rule die in the shape of a fish (long dimension about 5") is placed on top of the layers of nylon and beneath the head of the die press. The head of the die press is then brought down onto the steel-rule die, whereupon it cuts through the eight layers of fabric in a single strike to yield eight pieces of fish-shaped nylon fabric. The pieces are referred to as "cut halves."

Two cut halves are then placed together such that they are superimposed. The two cut halves are then sewn together along their mutual perimeter, leaving a 1.5"-wide orifice for later insertion of a filling. The sewn material is then turned inside-out such that the sewing cannot be seen. Polyurethane foam which has been incorporated with Ultra-Fresh DM-50 antimicrobial agent (Carpenter Company) is die-cut into small (2 cm×2 cm×2 cm) cubes. About fifty of these cubes are inserted into the nylon cover structure; and the aperture is then sewn closed.

EXAMPLE NO. 20

The cover or containment structure is made from a denim fabric. Eight rolls are suspended on a rack, and the fabric is pulled from the rolls in tandem and fed onto the bed of the die-cutting press. The same die as used in Example No. 4 is placed on top of the layers of denim and beneath the head of the die press. The head of the die press is then brought down onto the steel-rule die, whereupon it cuts through the eight layers of denim in a single strike to yield eight pieces of bone-shaped denim fabric. The pieces are referred to as "cut halves."

Two cut halves are then placed together such that they are superimposed. The two cut halves are then sewn together along their mutual perimeter, leaving a 1.5"-wide orifice for later insertion of a filling. The sewn material is then flipped inside-out such that the sewing cannot be seen. The structure is to be filled to a volume density of 3.2%. About 40 gm of Polyfill antibacterial fiber fill (100% polyester fiber treated with Aegis Microbe-Shield; available from Fairfield) is inserted through the aperture, which is then sewn closed.

Whereas the invention has been described with reference to the manufacture of a pet article, toys for humans can also be made in accordance with the inventions. When toys are intended for humans, the amount of anti-microbial agent can be reduce somewhat.

While particular embodiments of the invention have been shown, it will be understood, of course, that the invention is not limited thereto since modifications can be made by those skilled in the art, particularly in light of the foregoing teachings. Reasonable variation and modifications are possible within the scope of the foregoing disclosure of the invention without departing from the spirit of the invention.

What is claimed is:

1. A textile-based amusement article to be played with, enticed or retrieved by a domestic animal comprising:
    an outer textile casing formed of a tough, chew-resistant material defining a shape in the form of a small article for luring or being fetched by the domestic animal and comprising a high-pile component attached to a backing material to form an artificial fleece, the material formed in two layers sewn together at the edges with the high-pile component outwardly; and an effective amount of a microbe-cidal agent applied to the textile casing, wherein the microbe-cidal agent is non-toxic and non-carcinogenic when ingested by domestic animals at the levels used in the amusement article.

2. A textile-based amusement article according to claim 1 wherein the textile casing comprises fibers selected from the group consisting of acrylics, polyester, nylon, olefin polymers, triacetate, rubber and spandex fibers.

3. A textile-based amusement article according to claim 1 wherein the outer textile casing is treated with a compound to impart at least one of low surface energy, non-hydrophilic properties, antistatic properties and antiadhesion properties.

4. A textile-based amusement article according to claim 1 wherein the outer textile casing comprises an outer fabric layer and the microbe-cidal agent comprises a microbe-impenetrable laminate on an inner surface of the outer fabric layer.

5. A textile-based amusement article according to claim 4 wherein the microbe-impenetrable laminate comprises a thermoplastic film or latex polymer.

6. A textile-based amusement article according to claim 5 wherein the microbe-cidal agent is applied to or incorporated into the thermoplastic film or latex polymer.

7. A textile-based amusement article according to claim 1 and further comprising an odor-absorbing agent selected from at least one of an activated carbon and a zeolite compound.

8. A textile-based amusement article according to claim 1 wherein of the outer textile casing is impregnated with a flame resistant modacrylic polymer.

9. A textile-based amusement article to be played with, enticed or retrieved by a domestic animal comprising:

an outer textile casing formed of a tough, chew-resistant material defining a shape in the form of a small article for luring or being fetched by the domestic animal and comprising a high-pile component attached to a backing material to form an artificial fleece, the material formed in two layers sewn together at the edges with the high pile component outwardly; and a microbe-cidal agent applied to the textile casing in an effective amount and is selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof.

10. A textile-based amusement article according to claim 9 wherein the microbe-cidal agent is chlorine dioxide.

11. A textile-based amusement article according to claim 9 wherein the microbe-cidal agent is 2,4,4'-trichloro-2'-hydroxydiphenol.

12. A textile-based amusement article according to claim 9 wherein the microbe-cidal agent is non-toxic and non-carcinogenic when ingested by domestic animals at the levels used in the amusement article.

* * * * *